US012172969B2

(12) United States Patent
Holl et al.

(10) Patent No.: US 12,172,969 B2
(45) Date of Patent: Dec. 24, 2024

(54) DEUTERATED SECNIDAZOLE FOR USE IN THE TREATMENT OF BACTERIAL VAGINOSIS AND METHODS AND USES THEREOF

(71) Applicant: EVOFEM BIOSCIENCES, INC., San Diego, CA (US)

(72) Inventors: Richard John Holl, Somerset, NJ (US); Kurt Nielsen, Somerset, NJ (US); James Garegnani, Somerset, NJ (US)

(73) Assignee: EVOFEM BIOSCIENCES, INC., San Diego, CA (US)

( * ) Notice: Subject to any disclaimer, the term of this patent is extended or adjusted under 35 U.S.C. 154(b) by 109 days.

(21) Appl. No.: 17/681,634

(22) Filed: Feb. 25, 2022

(65) Prior Publication Data

US 2022/0259156 A1    Aug. 18, 2022

Related U.S. Application Data

(63) Continuation of application No. 16/560,478, filed on Sep. 4, 2019, now abandoned.

(60) Provisional application No. 62/727,159, filed on Sep. 5, 2018.

(51) Int. Cl.
*C07D 233/94* (2006.01)
*A61K 31/4164* (2006.01)
*A61K 31/565* (2006.01)
*A61K 31/57* (2006.01)

(52) U.S. Cl.
CPC ........ *C07D 233/94* (2013.01); *A61K 31/4164* (2013.01); *A61K 31/565* (2013.01); *A61K 31/57* (2013.01)

(58) Field of Classification Search
CPC .................. A61K 31/4164; C07D 233/94
See application file for complete search history.

(56) References Cited

U.S. PATENT DOCUMENTS

| | | | |
|---|---|---|---|
| 4,765,978 A | 8/1988 | Abidi et al. | |
| 2016/0067218 A1 | 3/2016 | Pentikis et al. | |

FOREIGN PATENT DOCUMENTS

| | | | |
|---|---|---|---|
| WO | WO 95/26325 | * | 3/1995 |
| WO | 2018013625 A1 | | 1/2018 |
| WO | 2020051216 A1 | | 3/2020 |

OTHER PUBLICATIONS

Adepu et al. (European Journal of Biomedical and Pharmaceutical Sciences vol. 4 (11), p. 587-592 (2017).*
P.A.B. Montovani et al. (Brazilian Journal of Pharmaceutical Sciences 2009, vol. 45 (4), p. 687-692).*
Marcilio et al. (Biosci. J., Uberlandia, v. 33, n. 5, p. 1351-1361 (2017)).*
Gillis et al. (Drugs, vol. 51 (4):621-638 (1996).*
FDA Solosec (secnidazole) Oral Granules Approval (available online since Sep. 15, 2017 at https://www.accessdata.fda.gov).*
Jeffery et al. (Clinical Biochemistry 50 (2017) 323-330).*
Miyano (J. Heterocycl. Chem. 1982, vol. 19 (3); 659-661).*
Kushner et al. (Canadian Journal of Physiology and Pharmacology, 77(2), 79-88, 1999).*
Foster (TIPS) (Trends in Pharmacological Sciences, 5(12), 524-527, 1984).*
Jordan, V. C. Nature Reviews: Drug Discovery, 2, 2003, pp. 205-213).*
Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
B. Rodriguez-Spong et al. (Advanced Drug Delivery Reviews, 2004, 56, p. 263)).*
Nyirjesy (Future Microbiology (2018) 13(5), 507-524).*
Shimodaira et al.—JP2009242343—(2009) with US counterpart US2010/0331540.*
Montovani, Patricia A. B., et al., "Bioavailability of two oral formulas of secnidazole in healthy volunteers, Brazilian Journal of Pharmaceutical Sciences", vol. 45(4):687-692 (2009).
Marcilio, M.R., et al., "Determination and Validation of Secnidazole in Tables by UV Spectrophotometric", Bioscience Journal, Uberlandia, vol. 33(5):1351-1361 Sep./Oct. 2017.
Kushner, D.J., et al., "Pharmacological uses and perspectives of heavy water and deuterated compounds", Canadian Journal of Physiology and Pharmacology, vol. 77(2):79-88 Feb. 1999.
Jeffery, J., et al., Development and validation of a liquid chromatography tandem mass spectrometry assay for the measurement of faecal metronidazole, Clinical Biochemistry, vol. 50:323-330 (2017).
Miyano, M., et al., "Preparation of 1-Hydroxyethyl-2-trideuteriomethyl-5-nitroimidazole", Journal Heterocyclic Chemistry, vol. 19:659 (1982).
Aug. 30, 2022 First Examination Report issued by the Indian Intellectual Property Office for Indian Patent Application No. 202117013320.
Foster, Allan B., "Deuterium isotope effects in studies of drug metabolism", Trends in Pharmaceutical Sciences, 524:527 (1984).
"Lupin Announces FDA Approval of Supplemental New Drug Application for SOLOSEC® (secnidazole) for the Treatment of Trichomoniasis", Biospace https://www.biospace.com/article/releases/lupin-announces-fda-approval-of-supplemental-new-drug-application-for-solosec-secnidazole-in-adolescents-for-both-the-treatment-of-bacterial-vaginosis-in-females-and-trichomoniasis/ (retrieved Aug. 1, 2021) 18 pages.
Gillis, J.C., et al., "Secnidazole: A Review of its Antimicrobial Activity, Pharmacokinetic Properties and Therapeutic Use in the Management of Protozoal Infections and Bacterial Vaginosis", Drugs, vol. 51(4):621-638 (1996).

(Continued)

*Primary Examiner* — Valerie Rodriguez-Garcia
(74) *Attorney, Agent, or Firm* — Procopio, Cory, Hargreaves & Savitch LLP

(57) ABSTRACT

The present invention is related to deuterated secnidazole, a prodrug thereof, a hydrate thereof, a solvate thereof, a polymorph thereof, or a pharmaceutically acceptable salt thereof and its use for the treatment of bacterial vaginosis or trichomoniasis in a subject in need thereof. The present invention is also related to pharmaceutical compositions and methods and uses of treating bacterial vaginosis, trichomoniasis, amoebiasis, giardiasis, or a combination thereof.

23 Claims, 1 Drawing Sheet

(56) References Cited

OTHER PUBLICATIONS

Videau, D., et al., "Secnidazole: A 5-nitroimidazole derivative with a long half-life", British Journal of Venereal Diseases, vol. 54:77-80 (1978).

Bohbot, J.M., et al., "Treatment of Bacterial Vaginosis: A Multicenter, Double-Blind, Double-Dummy, Randomised Phase III Study Comparing Secnidazole and Metronidazole", Infectious Diseases in Obstetrics and Gynecology, vol. 2010, Art. ID 705692, pp. 1-6 (2010).

Frydman, A.M., et al., "A review of the pharmacokinetics of secnidazole in man", The 16th International Congress of Chemotherapy, vol. 2:445.1-445.3 (1989).

Meunier, B., et al., "Mechanism of Oxidation Reactions Catalyzed by Cytochrome P450 Enzymes", Chemical Reviews, vol. 104(9):3947-3980 (2004).

Adepu, R., et al., "A Novel Method for The Determination of Secnidazole in Human Plasma by Using Liquid Chromatography-Electro Sprays Ionization Tandem Mass Spectrometry", European Journal of Biomedical and Pharmaceutical Sciences, vol. 4(11):587-592 (2017).

Mottier, P., et al., "Analysis of Four 5-Nitroimidazoles and Their Corresponding Hydroxylated Metabolites in Egg, Processed Egg, and Chicken Meat by Isotope Dilution Liquid Chromatography Tandem Mass Spectrometry", Journal of Agricultural and Food Chemistry, vol. 54(6):2018-2026 (2006).

Eiros, Hanna-Kirsti S., et al., "Structural Basis of 5-Nitroimidazole Antibiotic Resistance: The Crystal Structure of NimA From Deinococcus Radiodurans", The Journal of Biological Chemistry, vol. 279(53):55840-55849 (2004).

Berge, S. M., et al., "Pharmaceutical Salts", Journal of Pharmaceutical Sciences, vol. 66(1):1-19 (1977).

Rautio, J., et al., "The expanding role of prodrugs in contemporary drug design and development", Nature Reviews Drug Discovery, vol. 17:559-587 (2018).

Clas, Sophie-Dorothee, et al., "Chemistry-enabled drug delivery (prodrugs): recent progress and challenges", Drug Discovery Today, vol. 19(1):79-87 (2014).

Rautio, J., et al., "Prodrugs: design and clinical applications", Nature Reviews Drug Discovery, vol. 7:255-270 (2008).

Buteau, Kristen C."Deuterated Drugs: Unexpectedly Nonobvious?", 10 J. High Tech L. 22 (2009).

Howland, Robert H., MD, "Deuterated Drugs", Journal of Psychosocial Nursing and Mental Health Services, 53(9), 16-16 (2015).

Timmins, G.S., "Deuterated drugs; updates and obviousness analaysis", Expert Opinion on Therapeutic Patents, 27:12, 1353-1361 (2017), DOI:10.1080/13543776.2017.1378350.

Hangargekar, S. R., et al, "Formulation and Evaluation of Guar Gum Based Colon Targeted Tablets of Secnidazole and Its β-Cyclodextrin Complex to Treat Amoebiasis", International Journal of Pharmacy and Pharmaceutical Sciences, vol. 3, Suppl 4, (2011).

Nov. 12, 2019 International Search Report issued by the International Searching Authority for PCT International Application No. PCT/US19/49544.

Nov. 12, 2019 The Written Opinion of the International Searching Authority for PCT International Application No. PCT/US19/49544.

* cited by examiner

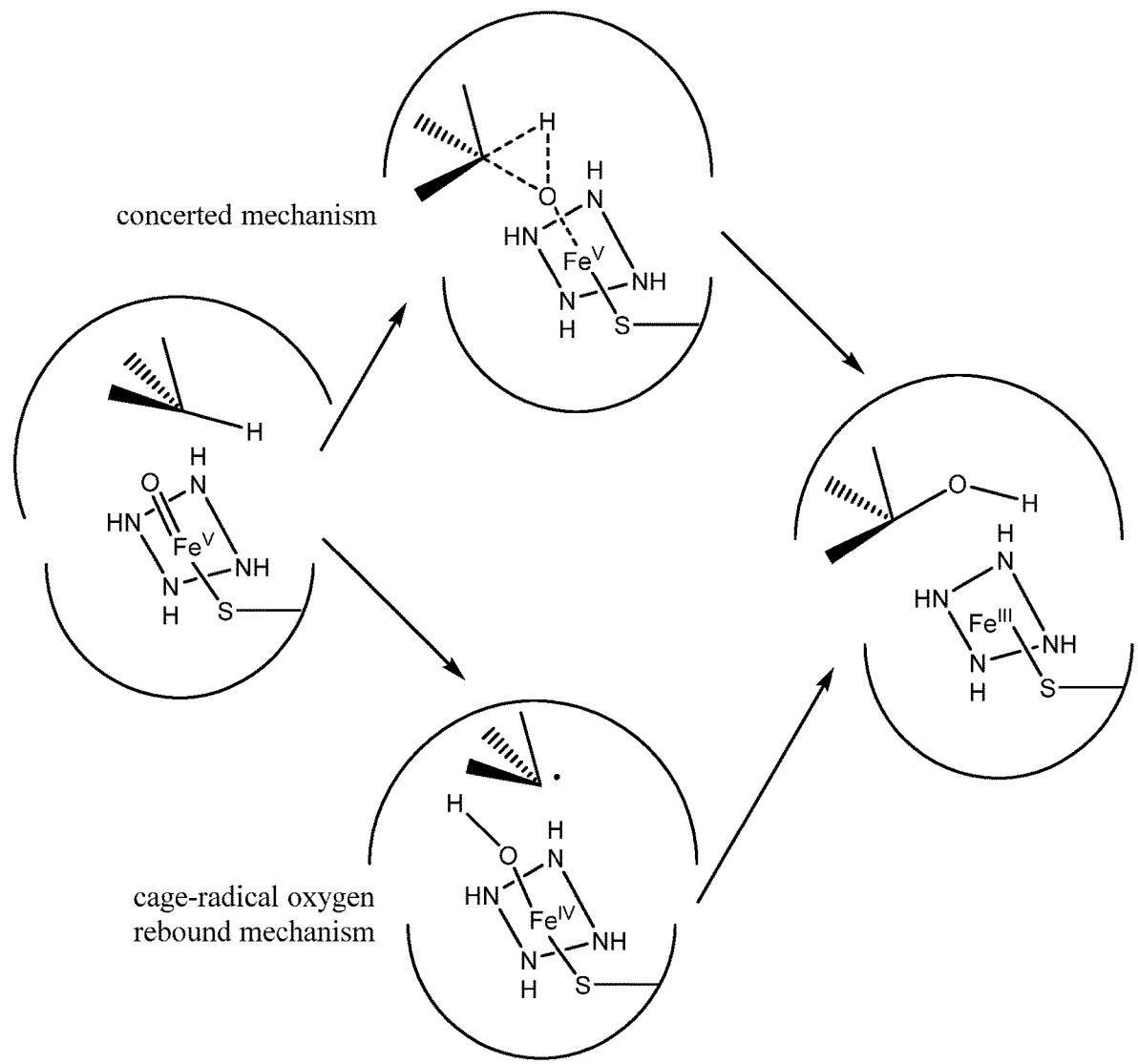

DEUTERATED SECNIDAZOLE FOR USE IN THE TREATMENT OF BACTERIAL VAGINOSIS AND METHODS AND USES THEREOF

CROSS-REFERENCE TO RELATED APPLICATION

This application is a continuation of U.S. patent application Ser. No. 16/560,478, filed on Sep. 4, 2019, which claims priority in and to U.S. Provisional Application No. 62/727,159, filed Sep. 5, 2018, which is hereby incorporated by reference herein in its entirety.

FIELD OF THE INVENTION

The present invention relates to deuterated secnidazole, pharmaceutical compositions including deuterated secnidazole, and methods of treating bacterial vaginosis or trichomoniasis using deuterated secnidazole or pharmaceutical compositions including deuterated secnidazole.

All references and products cited within this application and their disclosures therein are incorporated by reference herein in their entirety.

BACKGROUND

Secnidazole, a second generation 5-nitroimidazole, is a well-known antiprotozoal and anti-microbial drug (Gillis and Wiseman, "Secnidazole: A Review of its Antimicrobial Activity, Pharmacokinetic Properties, and Therapeutic Use in the Management of Protozoal Infections and Bacterial Vaginosis," *Drugs*, 51(4), 621-638 (1996)). Secnidazole is particularly effective in treatment of amoebiasis, giardiasis, trichomoniasis, and bacterial vaginosis. It is rapidly and completely absorbed after oral administration and has a terminal elimination half-life of about 17 to about 29 hours.

Secnidazole enters in to bacterial cell as a prodrug without antimicrobial activity and is converted into its active form in vivo via reduction of its nitro group to radical anions by bacterial enzymes. The radical anions are thought to interfere with bacterial DNA synthesis resulting in the antimicrobial activity. Because of its antimicrobial activity and long terminal elimination half-life, secnidazole can be administered as a single dose for the treatment of bacterial vaginosis (Videau, et al., "Secnidazole: A 5-nitroimidazole Derivative With a Long Half-life," *Brit. J. Venereal Diseases*, 54, 77-80 (1978); Gillis and Wiseman, "Secnidazole: A Review of its Antimicrobial Activity, Pharmacokinetic Properties, and Therapeutic Use in the Management of Protozoal Infections and Bacterial Vaginosis," *Drugs*, 51(4), 621-638 (1996); Bohbot et al., "Treatment of Bacterial Vaginosis: A Multicenter, Double-Blind, Double-Dummy, Randomised Phase III Study Comparing Secnidazole and Metronidazole," *Infect. Dis. Obstet. Gynecol.* vol. 2010, Article ID 705692, 6 pages, (2010)). Secnidazole is mainly metabolized via hydroxylation and glucuroconjugation in the liver and 50% of secnidazole is excreted intact in the urine (Frydman et al., "A Review of the Pharmacokinetics of Secnidazole in Man," 16th International Congress of Chemotherapy, 2, 445.1-445.3 (1989)).

Enzymes, such as, cytochrome $P_{450}$, esterases, proteases, reductases, dehydrogenases, and monoamine oxidases, help convert drugs to more polar intermediates or metabolites for renal excretion from an subject's body. These metabolic reactions involve oxidation of carbon-hydrogen (C—H) bond to either a carbon-oxygen (C—O) bond or a carbon-carbon (C—C) bond. If a drug is oxidized and eliminated rapidly from the subject's body, then often the drug will require administration of multiple or high doses in order to be efficacious.

Deuteration of drug molecules has been used before to improve pharmacokinetics ("PK"), pharmacodynamics ("PD"), and toxicity profiles. For example, deuteration was used to decrease the hepatotoxicity of halothane, presumably by limiting the production of reactive species such as trifluoroacetyl chloride. However, deuteration cannot be applied to every drug to achieve improved PK, PD, or toxicity profiles. For example, addition of deuterium to a drug molecule may lead to "metabolic switching." Metabolic switching can lead to production of new metabolites and/or change the fraction of known metabolites. This new metabolic profile, due to metabolic switching, may produce more adverse effects in a subject.

Incorporation of a heavy atom, e.g., substitution of deuterium (also known as the symbol "D" or "$^2$H") for hydrogen, can give rise to an isotope effect known as the kinetic isotope effect ("KIE"). KIE can cause metabolic switching. Upon deuterium substitution, some physicochemical properties of the deuterium-substituted molecule become different from those of its unsubstituted counterpart, but, the chemical and biological properties are the same with one important exception: because of the increased mass of the heavy isotope, any bond involving deuterium and another atom is stronger than the same bond between hydrogen and that atom. Therefore, any reaction in which the breaking of this bond is a rate limiting step, the reaction will proceed slower for the molecule with deuterium due to KIE. A reaction involving breaking a C-D bond can be up to 700 percent slower than a similar reaction involving breaking a C—H bond. This effect is usually insignificant if the substitution occurs at a location in the molecule that is a metabolically inert position of the molecule. However, incorporation of deuterium at the site of metabolism of a drug slows down its metabolism rate to a point where another metabolite produced by attack at a carbon atom, that is not substituted by deuterium, becomes the major pathway due to metabolic switching.

Prior literature on applying deuterium substitution strategies with various drug substances on the cytochrome $P_{450}$ enzyme system indicates a significant primary deuterium KIE can occur. The key determinant of whether the primary deuterium KIE would be present in the metabolism of a deuterated secnidazole is whether a C—H bond breaking step is rate-limiting in the metabolism of secnidazole.

Secnidazole has two positions that have sp3 hybridized C—H bonds, both of which are susceptible to oxidation reactions catalyzed by cytochrome $P_{450}$ enzymes (Frydman et al., "A Review of the Pharmacokinetics of Secnidazole in Man," 16th *International Congress of Chemotherapy* 2, 445.1-445.3 (1989)). As shown in FIG. 1, hydroxylation of an sp3 C—H bond is one of the ways in which CYP3A4 (and cytochrome $P_{450}$ oxygenases) affects its ligand (Meunier et al., "Mechanism of Oxidation Reactions Catalyzed by Cytochrome p450 Enzymes," *Chem. Rev.*, 104(9), 3947-3980 (2004)).

Because secnidazole has two C—H bonds that are susceptible to oxidation reactions, a primary deuterium KIE would be present and may be rate-limiting in the metabolism of a deuterated secnidazole. A more pronounced primary deuterium KIE will occur if deuterium replaces hydrogen on the secnidazole molecule in locations that are involved in C—H covalent bond breakage.

Deuterium substitution of a drug can also alter its physicochemical properties such as pKa and lipid solubility. These changes may influence the fate of the drug at different steps along its passage through the body, e.g., absorption, distribution, metabolism or excretion of a drug can be changed.

In 2017, SOLOSEC® (secnidazole, 2 g oral granules) was approved for the treatment of bacterial vaginosis in adult women by the Food and Drug Administration ("FDA"). Solosec™ has enhanced pharmacokinetic properties that enable its delivery and efficacy in a single dose. There are, however, certain adverse reactions reported for SOLOSEC®, such as, vulvo-vaginal candidiasis, headache, nausea, dysgeusia, vomiting, diarrhea, abdominal pain, and vulvovaginal pruritus (see Prescribing Information for SOLOSEC®).

Accordingly, there is a pending need in the medical and pharmaceutical arts to develop treatment for diseases, such as, bacterial vaginosis or trichomoniasis, where, e.g., the dose of secnidazole can be lowered to reduce adverse effects in patients without affecting its efficacy.

The present invention is directed to overcoming these and other deficiencies in the art.

SUMMARY

In consideration of the above problems, in accordance with one aspect disclosed herein, a compound of formula I, a prodrug thereof, a hydrate thereof, a solvate thereof, a polymorph thereof, or a pharmaceutically acceptable salt thereof. The compound of formula I is represented by the chemical structure shown below:

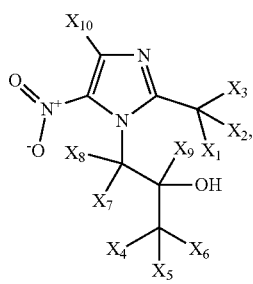

(I)

wherein $X_1$ to $X_{10}$ are independently selected from the group consisting of hydrogen (H) and deuterium (D), and at least one of $X_1$ to $X_{10}$ is deuterium.

In accordance with another aspect disclosed herein, a pharmaceutical composition including (a) the compound of formula I, a prodrug thereof, a hydrate thereof, a solvate thereof, a polymorph thereof, a pharmaceutically acceptable salt thereof, or a combination thereof, and (b) at least one pharmaceutically acceptable carrier. In certain embodiments, the pharmaceutical composition further comprises one or more pharmaceutically acceptable excipient.

In accordance with another aspect disclosed herein, a compound of formula I, a prodrug thereof, a hydrate thereof, a solvate thereof, a polymorph thereof, or a pharmaceutically acceptable salt thereof for use as a medicament. In a certain embodiments, the compound of formula I, the prodrug thereof, the hydrate thereof, the solvate thereof, the polymorph thereof, or the pharmaceutically acceptable salt thereof for use in the treatment of bacterial vaginosis ("By") or trichomoniasis.

In accordance with another aspect disclosed herein, a method for treating bacterial vaginosis, trichomoniasis, amoebiasis, giardiasis, or a combination thereof in a subject in need thereof. This method includes selecting the subject in need of treatment for bacterial vaginosis, trichomoniasis, amoebiasis, giardiasis, or a combination thereof and administering to the subject a therapeutically effective amount of a compound of formula I, a prodrug thereof, a hydrate thereof, a solvate thereof, a polymorph thereof, or a pharmaceutically acceptable salt thereof.

BRIEF DESCRIPTION OF THE DRAWINGS

FIG. 1 depicts the mechanism for the hydroxylation of an sp3 C—H bond.

DETAILED DESCRIPTION

The present invention is not limited to particular processes, compounds, or methodologies described, as these may vary. The terminology used in the description is for the purpose of describing particular versions or embodiments only, and is not intended to limit the scope of the present invention. Unless defined otherwise, all technical and scientific terms used herein have the same meanings as commonly understood by one of ordinary skill in the art. Any methods and materials similar or equivalent to those described herein can be used in the practice or testing of embodiments of the invention, the preferred methods, devices, and materials described herein.

Secnidazole is a second-generation 5-nitroimidazole antimicrobial that is structurally related to 5-nitroimidazoles, including, metronidazole and tinidazole, but displays improved oral absorption and longer terminal elimination half-life as compared to other antimicrobial agents in this class. It is also known as 1-(2-hydroxypropyl)-2-methyl-5-nitromidazole or 1-(2-methyl-5-nitro-1H-imidazol-1-yl)propan-2-ol and has the following chemical structure:

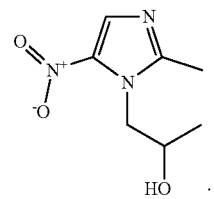

Secnidazole d-6 has been used as an internal standard for secnidazole spectroscopic detections. Deuterated 5-nitroimidazole was utilized as an internal standard for spectroscopic analysis of samples (Adepu et al., "A Novel Method for the Determination of Secnidazole in Human Plasma by Using Liquid Chromatography-Electro Sprays Ionization Tandem Mass Spectrometry," *Eur. J. Biomed. Pharma. Sci.,* 4(11): 587-592 (2017)). Deuterated internal standards, e.g., dimetridazole-d3, ronidazole-d3, ipronidazole-d3, DMZOH-d3, and IPZOH-d3 are also known (Mottier et al., "Analysis of Four 5-nitroimidazoles and Their Corresponding Hydroxylated Metabolites in Egg, Processed Egg, and Chicken Meat by Isotope Dilution Liquid Chromatography Tandem Mass Spectrometry," *J. Agric. Food Chem.* 54(6):2018-2026 (2006)).

Deuteration of secnidazole involves deuterium enrichment, in place of hydrogen atoms, on secnidazole with deuterium atoms—a heavier, nonradioactive isotope of hydrogen. Deuterium enrichment on certain hydrogen positions in secnidazole molecule is also referred to, herein, as replacement of hydrogen with deuterium.

Deuteration can slow chemical reactions of compounds due to a chemical phenomenon called kinetic isotope effect ("KIE"). Replacement of hydrogen in a secnidazole molecule with deuterium can result in higher dissociation energies, slower chemical reaction rates, and increased kinetic stability. Slower chemical reaction rate of deuterated secnidazole results in slower metabolism after the drug is administrated. For instance, non-deuterated secnidazole has a terminal elimination half-life of between 17 to 29 hours. An increase in secnidazole elimination half-life after administration can be achieved by deuteration of secnidazole molecule due to KIE.

Depending on the extent of KIE, the elimination half-life of deuterated secnidazole may be doubled compared to non-deuterated secnidazole. Increases in secnidazole elimination half-life of between about 29 to 58 hours upon deuteration may be possible with a preferred range of between about 34 to 58 hours.

An increase in the elimination half-life of secnidazole via deuteration can result in lowering of the dose needed for treatment of diseases, such as, bacterial vaginosis, trichomoniasis, amoebiasis, and giardiasis.

Also, deuterated secnidazole can exhibit antimicrobial activity since secnidazole's antimicrobial activity is caused by reduction of secnidazole's nitro group to radical anions by bacterial enzymes (Leiros et al., "Structural Basis of 5-nitroimidazole Antibiotic Resistance: The Crystal Structure of NimA from *Deinococcus radiodurans*," *J. Biol. Chem.* 279(53):55840-9 (2004)). Such reduction of secnidazole's nitro group to radical anions does not involve breaking of a C—H bond, therefore, deuteration would not affect antimicrobial activity of secnidazole.

Because deuteration causes an increase in elimination half-life of secnidazole while exhibiting (e.g., maintaining or increasing) antimicrobial activity, lower dosages of deuterated secnidazole can be used for treatment of diseases, such as, amoebiasis, giardiasis, bacterial vaginosis, and trichomoniasis as compared to non-deuterated secnidazole. Use of a lower dosage of deuterated secnidazole, as compared to non-deuterated secnidazole, leads to reduction in adverse effects (toxicity) in patients and solves problems associated with known treatment methods that use secnidazole. Moreover, use of a lower dose solves many technical and manufacturing problems. For example, a lower dose is easier to solubilize and is therefore less likely to give rise to problems associated with highly concentrated compositions, such as, solubility issues, precipitation of one or more components present in the composition, or difficulties in finding an appropriate composition of excipients that provide suitable physical/chemical properties for the drug.

For purposes of the present invention as disclosed and described herein, the following terms and abbreviations are defined as follows.

As used herein, the singular forms "a", "an" and "the" include plural reference unless the context clearly dictates otherwise.

As used herein, the term "about" as used herein, is intended to qualify the numerical values which it modifies, denoting such a value as variable within a margin of error. When no particular margin of error, such as a standard deviation to a mean value, is recited, the term "about" means plus or minus 10% of the numerical value of the number with which it is being used. Therefore, e.g., about 50% means in the range of 45%-55%.

When ranges of values are disclosed, and the notation "from $n_1$ . . . to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium" when used to describe an atom or the term "is/are deuterated" when used to describe an atom or the symbol "D" when used to represent a given position in a drawing of a molecular structure means that the specified position or atom is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

As used herein, the term "secnidazole" and "non-deuterated secnidazole" are used interchangeably and refer to a secnidazole molecule where the percentages of various isotopes are substantially the same as naturally occurring percentages unless the term "secnidazole" is appended to "deuterated," e.g., as in "deuterated secnidazole." The term "deuterated secnidazole" as used herein, and in the appended claims, refers to secnidazole where one or more position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

Asymmetric centers exist in the compounds disclosed herein. These centers are designated by the symbols "R" or "S" depending on the configuration of substituents around the chiral carbon atom. For example, secnidazole has one asymmetric carbon:

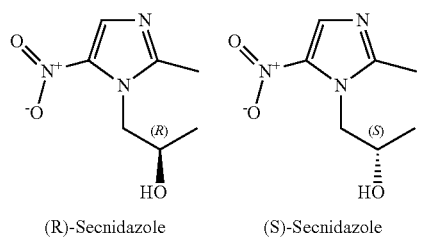

(R)-Secnidazole     (S)-Secnidazole

It should be understood that the present invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, Entgegen (E), and Zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

As used herein, the term "patient" and "subject" are interchangeable and may be taken to mean any living organism that may be treated with compounds/compositions of the present invention. As such, the terms "patient" and "subject" may include, but is not limited to, any non-human mammal, primate or human. In some embodiments, the "patient" or "subject" is an adult, child, infant, or fetus. In some embodiments, the term "patient" or "subject" is a human. In some embodiments, the term "patient" or "subject" is a mammal, such as mice, rats, other rodents, rabbits, dogs, cats, swine, cattle, sheep, horses, primates, or humans.

In each of the embodiments disclosed herein, the compounds, pharmaceutical compositions, and methods may be utilized with or on a subject in need of such treatment, which may also be referred to as "in need thereof." As used herein, the phrase "in need thereof" means that the subject has been identified as having a need for the particular method or treatment or that the treatment has been given to the subject for that particular purpose.

The terms "treat," "treating," and "treatment" are meant to include alleviating or abrogating a disease/disorder or one or more of the symptoms associated with a disease/disorder; or alleviating or eradicating the cause(s) of the disease/disorder itself. As used herein, reference to "treatment" of a disease/disorder is intended to include prevention. The terms "prevent," "preventing," and "prevention" refer to a method of delaying or precluding the onset of a disease/disorder; and/or its attendant symptoms, barring a subject from acquiring a disease/disorder or reducing a subject's risk of acquiring a disease/disorder. The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

As used herein, the term "therapeutic" means an agent utilized to treat, combat, ameliorate or prevent an unwanted disease, condition or disorder of a patient.

As used herein, the term "administering" when used in conjunction with a therapeutic means to administer a therapeutic directly or indirectly into or onto a target tissue or to a patient whereby the therapeutic locally or systemically affects the tissue or the patient. "Administering" a composition may be accomplished by oral administration, injection, infusion, inhalation, absorption or by any method in combination with other known techniques. "Administering" may include the act of self-administration or administration by another person such as by a health care provider.

As used herein, the term "pharmaceutical composition" means a composition including at least one or more active ingredients, whereby the composition is amenable to investigation for a specified, efficacious outcome in a mammal (for example, without limitation, a human). Those of ordinary skill in the art will understand and appreciate the techniques appropriate for determining whether the active ingredients of the pharmaceutical composition have a desired efficacious outcome based upon the needs of the artisan.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, Fla., 2004).

The terms "therapeutically effective amount" or "therapeutic dose" are used interchangeably and refer to the amount of an active agent or pharmaceutical compound or composition that elicits a clinical, biological or medicinal response in a tissue, system, animal, individual or human that is being sought by a researcher, veterinarian, medical doctor, or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experience or exhibited by the individual.

The term "pharmaceutically acceptable salt" for the purpose of present invention is meant to indicate, without any limitation, those salts which are within the scope of sound medical judgment, suitable for use in contact with the tissues of a patient, without undue toxicity, irritation, allergic response and the like, and are commensurate with a reasonable benefit/risk ratio. Pharmaceutically acceptable salts suitable for the present invention are well known in the art and described in, for instance, Berge et al., "Pharmaceutical Salts," *J. Pharm. Sci.*, 66(1):1-19 (1977). For example, in one embodiment, a pharmaceutically acceptable salt of the present invention can be any acid addition salt, preferably a pharmaceutically acceptable acid addition salt, including, but not limited to, halogenic acid salts such as hydrobromic, hydrochloric, hydrofloric and hydroiodic acid salt; an inorganic acid salt, such as, nitric, perchloric, sulfuric and phosphoric acid salt; an organic acid salt, such as, sulfonic acid salts (such as methanesulfonic, trifluoromethan sulfonic, ethanesulfonic, benzenesulfonic or p-toluenesufonic), acetic, malic, fumaric, succinic, citric, benzonic gluconic, lactic, mandelic, mucic, pamoic, pantothenic, oxalic and maleic acid salts; or an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

The term "prodrug" refers to a functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis (Rautio et al., "The Expanding Role of Prodrugs in Contemporary Drug Design and Development," *Nature Reviews Drug Discovery* 17:559-587 (2018); Clas et al., "Chemistry-enabled Drug Delivery (prodrugs): Recent Progress and Challenges," *Drug Discov. Today* 19:79-87 (2014); Rautio, *J. Prodrugs and Targeted Delivery*, Wiley-VCH Verlag GmbH & Co. KGaA (2011); Stella, V. J. et al. *Prodrugs: Challenges and Rewards* Vol. 1-2, Springer & AAPS Press (2007); Rautio, J. et al., "Prodrugs: design and clinical applications," *Nat. Rev. Drug Discov.* 7, 255-270 (2008)).

As used herein, the term "solvate" refers to a complex that is formed by combining the molecules or ions of a solvent with a compound. In other words, the term "solvate" refers to the complex that is obtained by the process of solvation where a solvent and a solute molecules reorganize into solvation complexes. The term "solvates" includes crystal forms containing either stoichiometric or nonstoichiometric amounts of a solvent.

As used herein, the term "hydrate" refers to a compound that absorbs water molecules from its environment and includes them as part of its structure. In some instances, the hydrates of organic compounds are such that the water chemically reacts with the organic compound. In some instances, the term "hydrate" includes a solvate where the incorporated solvent is water.

As used herein, the term "polymorph" refers to crystalline polymorphic forms and amorphous polymorphic forms of a compound. Crystalline polymorphs have different arrangements and/or conformations of the molecules in crystal lattice. Amorphous polymorphs consist of disordered arrangements of molecules that do not possess a distinguishable crystal lattice.

As used herein, the term "elimination half-life" refers to a period of time required for the plasma concentration or the amount of drug in the subject to be reduced by one-half. This reduction can be caused by the drug being metabolized and eliminated from the subject.

In accordance with an aspect of the present invention, a compound of formula I, a prodrug thereof, a hydrate thereof, a solvate thereof, a polymorph thereof, or a pharmaceutically acceptable salt thereof. The compound of formula I is represented by the chemical structure shown below:

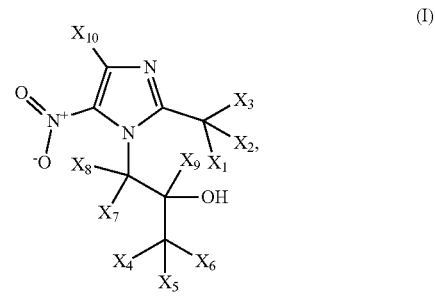

(I)

wherein $X_1$ to $X_{10}$ are independently selected from the group consisting of hydrogen and deuterium, and at least one of $X_1$ to $X_{10}$ is deuterium.

Certain embodiments of the present invention include a compound of formula I, wherein one or more of $X_4$, $X_5$, $X_6$, $X_7$, $X_8$, and $X_9$ is deuterium; one or more of $X_1$, $X_2$, and $X_3$ is deuterium; $X_{10}$ is deuterium; or combinations thereof. Other embodiments of the present invention include compounds of formula I, wherein $X_{10}$ is deuterium and $X_1$ to $X_9$ are hydrogen; $X_{10}$ is hydrogen and $X_1$ to $X_9$ are deuterium; $X_1$ to $X_{10}$ are deuterium; $X_1$, $X_2$, and $X_3$ are deuterium and $X_4$, $X_5$, $X_6$, $X_7$, $X_8$, and $X_9$ are hydrogen; $X_1$, $X_2$, and $X_3$ are hydrogen and $X_4$, $X_5$, $X_6$, $X_7$, $X_8$, and $X_9$ are deuterium; $X_1$, $X_2$, and $X_3$ are deuterium and $X_{10}$ is hydrogen; or $X_5$, $X_6$, $X_7$, $X_8$, and $X_9$ are deuterium and $X_{10}$ is hydrogen.

The present invention includes any compound obtained by replacing any or all of the ten hydrogen atoms present in non-deuterated secnidazole with deuterium. Hydrogen atoms are present on the secnidazole molecule in three locations: 1) six hydrogen atoms on the hydroxypropyl side-chain from N3 of the imidazole ring; 2) three hydrogen atoms on the methyl side-chain from C2 of the imidazole ring; and 3) one hydrogen atom on C5 in the imidazole ring. Deuterated secnidazole can be obtained by replacement of one or more of the hydrogen atoms present in any or all of the three locations on secnidazole with deuterium.

In some embodiments, the present invention includes deuterated secnidazole or a combination of deuterated secnidazole with non-deuterated secnidazole. In other embodiments, deuterated secnidazole is obtained by replacing one hydrogen, two hydrogens, three hydrogens, four hydrogens, five hydrogens, six hydrogens, seven hydrogens, eight hydrogens, nine hydrogens, or all ten hydrogens of non-deuterated secnidazole with deuterium. In one embodiment, one or more hydrogen is replaced with deuterium at any location on the hydroxypropyl or methyl side-chains. In another embodiment, all hydrogen atoms present in the hydroxypropyl or methyl side-chains are replaced by deuterium atoms. In another embodiment, one or all hydrogen atoms on the methyl side-chain are replaced with deuterium. In another embodiment, one or all hydrogen atoms on the hydroxypropyl side-chain are replaced with deuterium.

In a preferred embodiment, deuterium atoms replace all six hydrogen atoms on the hydroxypropyl side-chain of secnidazole. This form of secnidazole is also referred to as 1,1,1,2,3,3-hexadeuterio-3-(2-methyl-5-nitroimidazol-1-yl) propan-2-ol; Secnidazole-d6; α,2-Dimethyl-5-nitro-1H-imidazole-1-ethanol-d6; 1-(2-methyl-5-nitroimidazol-1-yl)-2-propanol-d6; Secnidazole-d6; 1-(2-methyl-5-nitro-1H-imidazol-1-yl)(2H6)propan-2-ol; 1-(2-methyl-5-nitroimidazol-1-yl)(2H6)propan-2-ol; flagentyl-d6; PM 185184-d6; RP 14539-d6.

An example of a secnidazole molecule with replacement of six (6) hydrogen atoms on the hydroxypropyl side-chain on N3 of imidazole ring with deuterium is provided below.

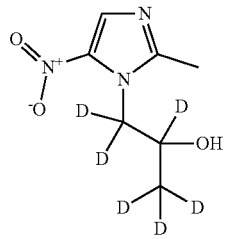

Another example of a secnidazole molecule with replacement of three (3) hydrogen atoms on the methyl side-chain of imidazole ring with deuterium is provided below.

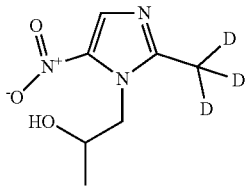

In accordance with another aspect of the present invention, a pharmaceutical composition including (a) the compound of formula I, a prodrug thereof, a hydrate thereof, a solvate thereof, a polymorph thereof, a pharmaceutically acceptable salt thereof, or a combination thereof, and (b) at least one pharmaceutically acceptable carrier.

In certain embodiments, the amount of compound of formula I, the prodrug thereof, the hydrate thereof, the solvate thereof, the polymorph thereof, or the pharmaceutically acceptable salt thereof in the pharmaceutical composition is from about 0.1 mg to about 2000 mg.

In some embodiments, the pharmaceutical composition of the present invention is in the form of a tablet, granules, microgranules, vaginal suppository, soft gelatin capsule, taste-masked tablet, taste-masked granules, taste-masked microgranules, or a combination thereof. In other embodiments, the pharmaceutical compositions of the present invention are in the form of a plurality of granules, a plurality of microgranules, a plurality of taste-masked granules, a plurality of taste-masked microgranules, or a combination thereof.

In certain embodiments, the pharmaceutical compositions of the present invention include at least one pharmaceutically acceptable excipient. The pharmaceutically acceptable excipient can be an inert core, a dispersion agent, a binding agent, a coating agent, a modified release coating agent, an anti-tacking agent, or a combination thereof.

In certain embodiments, the pharmaceutical compositions of the present invention are such that the elimination half-life of the compound of formula I, a prodrug thereof, a hydrate thereof, a solvate thereof, a polymorph thereof, or a pharmaceutically acceptable salt thereof is from about 29 hours to about 58 hours. In other embodiments, elimination half-life of the compound of formula I, a prodrug thereof, a hydrate thereof, a solvate thereof, a polymorph thereof, or a pharmaceutically acceptable salt thereof is from about 34 hours to about 58 hours.

Another aspect of the present invention includes a method for treating bacterial vaginosis, trichomoniasis, amoebiasis, giardiasis, or a combination thereof in a subject in need thereof. In another embodiment, the method includes selecting the subject in need of treatment for bacterial vaginosis, trichomoniasis, amoebiasis, giardiasis, or a combination thereof and administering to the subject a therapeutically effective amount of a compound of formula I, a prodrug thereof, a hydrate thereof, a solvate thereof, a polymorph thereof, or a pharmaceutically acceptable salt thereof. In another embodiment, the method includes selecting a subject in need of treatment for bacterial vaginosis, trichomoniasis, amoebiasis, giardiasis, or a combination thereof and administering, to the subject, a therapeutically effective amount of deuterated secnidazole, a combination of deuterated secnidazole with non-deuterated secnidazole, or pharmaceutically acceptable salts thereof. In another embodiment, a method of treating bacterial vaginosis, trichomoniasis, amoebiasis, giardiasis, or a combination thereof includes administering to the subject a compound of formula I, wherein one or more of $X_4$, $X_5$, $X_6$, $X_7$, $X_8$, and $X_9$ is deuterium; one or more of $X_1$, $X_2$, and $X_3$ is deuterium; $X_{10}$ is deuterium; or combinations thereof. Other embodiments include treating bacterial vaginosis, trichomoniasis, amoebiasis, giardiasis, or a combination thereof by administering compounds of formula I, wherein $X_{10}$ is deuterium and $X_1$ to $X_9$ are hydrogen; $X_{10}$ is hydrogen and $X_1$ to $X_9$ are deuterium; $X_1$ to $X_{10}$ are deuterium; $X_1$, $X_2$, and $X_3$ are deuterium and $X_4$, $X_5$, $X_6$, $X_7$, $X_8$, and $X_9$ are hydrogen; $X_1$, $X_2$, and $X_3$ are hydrogen and $X_4$, $X_5$, $X_6$, $X_7$, $X_8$, and $X_9$ are deuterium; $X_1$, $X_2$, and $X_3$ are deuterium and $X_{10}$ is hydrogen; or $X_5$, $X_6$, $X_7$, $X_8$, and $X_9$ are deuterium and $X_{10}$ is hydrogen. In another embodiment, the method of treating bacterial vaginosis, trichomoniasis, amoebiasis, giardiasis, or a combination thereof includes deuterated secnidazole or a combination of deuterated secnidazole with non-deuterated secnidazole. In another embodiment, deuterated secnidazole is obtained by replacing one hydrogen, two hydrogens, three hydrogens, four hydrogens, five hydrogens, six hydrogens, seven hydrogens, eight hydrogens, nine hydrogens, or all ten hydrogens of non-deuterated secnidazole with deuterium.

In another embodiment, a method of treating bacterial vaginosis, trichomoniasis, amoebiasis, giardiasis, or a combination thereof includes any compound obtained by replacing any or all of the ten hydrogen atoms present in non-deuterated secnidazole with deuterium. In another embodiment, a method of treating bacterial vaginosis, trichomoniasis, amoebiasis, giardiasis, or a combination thereof includes compounds where one or more hydrogen on non-deuterated secnidazole is replaced with deuterium at any location on the hydroxypropyl or methyl side-chains. In another embodiment, all hydrogen atoms present in the hydroxypropyl or methyl side-chains of non-deuterated secnidazole are replaced by deuterium atoms. In another embodiment, one or all hydrogen atoms on the methyl side-chain of non-deuterated secnidazole are replaced with deuterium. In another embodiment, one or all hydrogen atoms on the hydroxypropyl side-chain of non-deuterated secnidazole are replaced with deuterium. In a preferred embodiment, deuterium atoms replace all six hydrogen atoms on the hydroxypropyl side-chain of non-deuterated secnidazole.

In some embodiments, methods of treating bacterial vaginosis, trichomoniasis, amoebiasis, giardiasis, or a combination thereof are such that the subject is a human female or a pregnant human female. In some embodiments, the subject is a human. In other embodiments, the subject is a human female. In some embodiments, the human female is of an age ranging from a postmenarchal adolescent to a premenopausal woman. In some embodiments, the subject is an otherwise healthy female. In some embodiments, the subject is a pregnant female. In some embodiments, the subject is an otherwise healthy pregnant female. In some embodiments, the subject is a female with human immunodeficiency virus ("HIV"). In some embodiments, the subject is a female without HIV. In some embodiments, the subject is a pregnant female with HIV. In some embodiments, the subject has a sexual partner that is HIV positive. In some embodiments, the subject is a female with a sexually transmitted infection ("STI"). In some embodiments, the subject is a female without STI. In some embodiments, the subject is a pregnant female with STI. In some embodiments, the subject has a sexual partner that has STI. In some embodiments, the subject is a female having had 3 or fewer bacterial vaginosis, bacterial vaginosis, trichomoniasis, amoebiasis, giardiasis, or a combination thereof infections/episodes in the past 12 months. In some embodiments, the subject is a female having had 4 or more bacterial vaginosis, bacterial vaginosis, trichomoniasis, amoebiasis, giardiasis, or a combination thereof infections/episodes in the past 12 months.

In some embodiments, the subject is a female with confirmed bacterial vaginosis, trichomoniasis, amoebiasis, giardiasis, or a combination thereof. In some embodiments, the subject is a female with suspected bacterial vaginosis, trichomoniasis, amoebiasis, giardiasis, or a combination thereof. In some embodiments, the subject is a female with recurring bacterial vaginosis, trichomoniasis, amoebiasis, giardiasis, or a combination thereof. In some embodiments, a subject with recurring bacterial vaginosis, trichomoniasis, amoebiasis, giardiasis, or a combination thereof is a subject with 4 or more bacterial vaginosis infections within a twelve-month period. In some embodiments, the subject is a female with frequent bacterial vaginosis, trichomoniasis, amoebiasis, giardiasis, or a combination thereof infections. In some embodiments, a female with frequent bacterial vaginosis, trichomoniasis, amoebiasis, giardiasis, or a combination thereof infections is a female with 4 or more bacterial vaginosis, trichomoniasis, amoebiasis, giardiasis, or a combination thereof infections within a twelve-month period.

In some embodiments, the subject is a female presenting with an off-white (milky or gray), thin, homogeneous vaginal discharge, an odor, or a combination thereof. In some embodiments, the subject is a female presenting with abnormal vaginal discharge, a positive KOH Whiff test, vaginal fluid pH greater than or equal to 4.7, and the presence of "clue cells" greater than 20% of total epithelial cells (e.g., on microscopic examination of a vaginal saline wet mount), a positive 10% KOH Whiff test, or any combination thereof.

In some embodiments, the female presents with four Amsel criteria parameters and a gram stain slide Nugent score equal to, or higher than four on bacterial analysis of vaginal samples. In some embodiments, the four Amsel criteria parameters are abnormal vaginal discharge, a positive KOH Whiff test, vaginal fluid pH greater than or equal to 4.7, and the presence of clue cells greater than 20% of total epithelial cells.

In certain embodiments, the method of treating bacterial vaginosis, trichomoniasis, amoebiasis, giardiasis, or a combination thereof includes administering a therapeutically effective amount of the compound of formula I, a prodrug thereof, a hydrate thereof, a solvate thereof, a polymorph thereof, or a pharmaceutically acceptable salt thereof wherein the therapeutically effective amount is from about 0.1 mg to about 2000 mg, about 0.1 mg to about 1000 mg, or about 500 mg to about 1000 mg. In some embodiments, the therapeutically effective amount of the compound of formula I, a prodrug thereof, a hydrate thereof, a solvate thereof, a polymorph thereof, or a pharmaceutically acceptable salt thereof is administered as a single dose. In some embodiments, the therapeutically effective amount of the compound of formula I, a prodrug thereof, a hydrate thereof, a solvate thereof, a polymorph thereof, or a pharmaceutically acceptable salt thereof is administered orally.

In some embodiments, the method of treating bacterial vaginosis, trichomoniasis, amoebiasis, giardiasis, or a combination thereof includes administering the compound of formula I, a prodrug thereof, a hydrate thereof, a solvate thereof, a polymorph thereof, or a pharmaceutically acceptable salt thereof to the subject in the form of a tablet, granules, microgranules, vaginal suppository, soft gelatin capsule, taste-masked tablet, taste-masked granules, taste-masked microgranules, or a combination thereof. In other embodiments, the method includes administering the compound of formula I, a prodrug thereof, a hydrate thereof, a solvate thereof, a polymorph thereof, or a pharmaceutically acceptable salt thereof to the subject in the form of a plurality of granules, a plurality of microgranules, a plurality of taste-masked granules, a plurality of taste-masked microgranules, or a combination thereof.

In some embodiments, the method of treating bacterial vaginosis, trichomoniasis, amoebiasis, giardiasis, or a combination thereof includes administering the compound of formula I, a prodrug thereof, a hydrate thereof, a solvate thereof, a polymorph thereof, or a pharmaceutically acceptable salt thereof to the subject as a pharmaceutical composition. The pharmaceutical compositions used in the method of treating bacterial vaginosis, trichomoniasis, amoebiasis, giardiasis, or a combination thereof include at least one pharmaceutically acceptable excipient, at least one pharmaceutically acceptable carrier, or a combination thereof. The pharmaceutically acceptable excipient can be an inert core, a dispersion agent, a binding agent, a coating agent, a modified release coating agent, an anti-tacking agent, or a combination thereof.

In some embodiments, the method of treating bacterial vaginosis, trichomoniasis, amoebiasis, giardiasis, or a combination thereof includes the compound of formula I, a prodrug thereof, a hydrate thereof, a solvate thereof, a polymorph thereof, or a pharmaceutically acceptable salt thereof wherein the elimination half-life of the compound of formula I, the prodrug thereof, the hydrate thereof, the solvate thereof, the polymorph thereof, or the pharmaceutically acceptable salt thereof is from about 29 hours to about 58 hours. In some embodiments, the method of treating bacterial vaginosis, trichomoniasis, amoebiasis, giardiasis, or a combination thereof includes the compound of formula I, a prodrug thereof, a hydrate thereof, a solvate thereof, a polymorph thereof, or a pharmaceutically acceptable salt thereof wherein the elimination half-life of the compound of formula I, the prodrug thereof, the hydrate thereof, the solvate thereof, the polymorph thereof, or the pharmaceutically acceptable salt thereof is from about 34 hours to about 58 hours.

In some embodiments, a method of treating bacterial vaginosis, trichomoniasis, amoebiasis, giardiasis, or a combination thereof in a subject comprises co-administering to the subject a dose of a therapeutically effective amount of a compound of formula I, a prodrug thereof, a hydrate thereof, a solvate thereof, a polymorph thereof, or a pharmaceutically acceptable salt thereof and an additional compound selected from ethinyl estradiol ("EE2"), norethindrone ("NET"), or a combination thereof. In some embodiments, the additional compound is co-administered on the same day as the compound of formula I, a prodrug thereof, a hydrate thereof, a solvate thereof, a polymorph thereof, or a pharmaceutically acceptable salt thereof. In some embodiments, the additional compound is administered on a different day than the compound of formula I, a prodrug thereof, a hydrate thereof, a solvate thereof, a polymorph thereof, or a pharmaceutically acceptable salt thereof. In some embodiments, the administration of the compound of formula I, a prodrug thereof, a hydrate thereof, a solvate thereof, a polymorph thereof, or a pharmaceutically acceptable salt thereof to the subject does not affect the contraceptive efficacy of the additional compound.

In some embodiments, the diagnosis of bacterial vaginosis is confirmed by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, a positive 10% KOH Whiff test and a gram stain slide Nugent score equal to, or higher than four (4) on bacterial analysis of vaginal samples.

In some embodiments, suspected bacterial vaginosis is indicated by the presence of four (4) Amsel criteria parameters selected from an off-white (milky or gray), thin, homogeneous vaginal discharge, vaginal pH greater than or equal to 4.7, the presence of clue cells of greater than or equal to 20% of the total epithelial cells on microscopic examination of a vaginal saline wet mount, and a positive 10% KOH Whiff test.

In some embodiments, a method of treating bacterial vaginosis in a subject further comprises determining a post treatment clinical outcome. In some embodiments, a post treatment clinical outcome is indicative of a clinical outcome responder. Some embodiments further comprise determining a post-treatment clinical outcome. In some embodiments, a post-treatment clinical outcome of clinical cure is defined as a clinical outcome responder. In some embodiments, a clinical outcome responder is a subject with normal vaginal discharge, a negative KOH Whiff test, and clue cells less than or equal to 20% of the total epithelial cells on microscopic examination of a vaginal saline wet mount after treatment with the deuterated secnidazole formulations of the present invention. In some embodiments, a clinical outcome responder has a gram stain slide Nugent score of less than four (4) after treatment with a single dose of deuterated secnidazole. In yet other embodiments, a clinical outcome responder is a subject with normal vaginal discharge, a negative KOH Whiff test, clue cells less than 20% of total epithelial cells, and a gram stain slide Nugent score of less than four (4) after treatment with a single dose of deuterated secnidazole.

In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 to about 10 days after administration. In some embodiments, a post-treatment clinical outcome is observable after about 11 to about 20 days after administration. In some embodiments, a post-treatment clinical outcome is observable after about 21 to about 30 days after administration.

In some embodiments, a method of treating bacterial vaginosis, trichomoniasis, amoebiasis, giardiasis, or a combination thereof further comprises an alleviation of one or more symptoms of bacterial vaginosis, trichomoniasis, amoebiasis, giardiasis, or a combination thereof within up to about three days after administration to the subject. In some embodiments, a method of treating bacterial vaginosis, trichomoniasis, amoebiasis, giardiasis, or a combination thereof further comprises an alleviation of one or more symptoms of bacterial vaginosis, trichomoniasis, amoebiasis, giardiasis, or a combination thereof within up to about three days after administration to the subject. In some embodiments, the one or more symptoms include, but are not limited to, abnormal vaginal odor, abnormal vaginal discharge or a combination thereof. In some embodiments, alleviation refers to a lessening of the severity of one or more symptoms. In some embodiments, alleviation of one or more symptoms of bacterial vaginosis, trichomoniasis, amoebiasis, giardiasis, or a combination thereof occurs within about 24 hours after administration. In some embodiments, alleviation of one or more symptoms of bacterial vaginosis, trichomoniasis, amoebiasis, giardiasis, or a combination thereof occurs within about 48 hours after administration. In some embodiments, alleviation of one or more symptoms of bacterial vaginosis, trichomoniasis, amoebiasis, giardiasis, or a combination thereof occurs within about 72 hours after administration to the subject. In some embodiments, alleviation of one or more symptoms of bacterial vaginosis, trichomoniasis, amoebiasis, giardiasis, or a combination thereof occurs within about 96 hours after administration to the subject. In some embodiments, alleviation of one or more symptoms of bacterial vaginosis, trichomoniasis, amoebiasis, giardiasis, or a combination thereof occurs within about 120 hours after administration to the subject. In some embodiments, alleviation of one or more symptoms of bacterial vaginosis, trichomoniasis, amoebiasis, giardiasis, or a combination thereof occurs within about 168 hours after administration to the subject. In some embodiments, alleviation of one or more symptoms of bacterial vaginosis, trichomoniasis, amoebiasis, giardiasis, or a combination thereof occurs within about 7 to about 10 days after administration to the subject. In some embodiments, alleviation of one or more symptoms of bacterial vaginosis, trichomoniasis, amoebiasis, giardiasis, or a combination thereof occurs within about 11 to about 20 days after administration to the subject. In some embodiments, alleviation of one or more symptoms of bacterial vaginosis, trichomoniasis, amoebiasis, giardiasis, or a combination thereof occurs within about 21 to about 30 days after administration to the subject.

In some embodiments, a method of treating bacterial vaginosis, trichomoniasis, amoebiasis, giardiasis, or a combination thereof further comprises a resolution of one or more symptoms of bacterial vaginosis, trichomoniasis, amoebiasis, giardiasis, or a combination thereof within up to about seven days after administration to the subject. In some embodiments, a method of treating bacterial vaginosis, trichomoniasis, amoebiasis, giardiasis, or a combination thereof further comprises a resolution of one or more symptoms of bacterial vaginosis, trichomoniasis, amoebiasis, giardiasis, or a combination thereof within up to about seven days after administration to the subject. In some embodiments, the one or more symptoms include, but are not limited to, abnormal vaginal odor, abnormal vaginal discharge or a combination thereof. In some embodiments, resolution of one or more symptoms of bacterial vaginosis, trichomoniasis, amoebiasis, giardiasis, or a combination thereof occurs within about 24 hours after administration to the subject. In some embodiments, resolution of one or more symptoms of bacterial vaginosis, trichomoniasis, amoebiasis, giardiasis, or a combination thereof occurs within about 48 hours after administration. In some embodiments, resolution of one or more symptoms of bacterial vaginosis, trichomoniasis, amoebiasis, giardiasis, or a combination thereof occurs within about 72 hours after administration to the subject. In some embodiments, resolution of one or more symptoms of bacterial vaginosis, trichomoniasis, amoebiasis, giardiasis, or a combination thereof occurs within about 96 hours after administration to the subject. In some embodiments, resolution of one or more symptoms of bacterial vaginosis, trichomoniasis, amoebiasis, giardiasis, or a combination thereof occurs within about 120 hours after administration to the subject. In some embodiments, resolution of one or more symptoms of bacterial vaginosis, trichomoniasis, amoebiasis, giardiasis, or a combination thereof occurs within about 168 hours after administration to the subject. In some embodiments, resolution of one or more symptoms of bacterial vaginosis, trichomoniasis, amoebiasis, giardiasis, or a combination thereof occurs within about 7 to about 10 days after administration to the subject. In some embodiments, resolution of one or more symptoms of bacterial vaginosis, trichomoniasis, amoebiasis, giardiasis, or a combination thereof occurs within about 11 to about 20 days after administration to the subject. In some embodiments, resolution of one or more symptoms of bacterial vaginosis, trichomoniasis, amoebiasis, giardiasis, or a combination thereof occurs within about 21 to about 30 days after administration to the subject.

In some embodiments, a method of treating bacterial vaginosis, trichomoniasis, amoebiasis, giardiasis, or a combination thereof in a subject in need thereof further comprises administering a therapeutically effective amount of the compound of formula I, a prodrug thereof, a hydrate thereof, a solvate thereof, a polymorph thereof, or a pharmaceutically acceptable salt thereof to at least one of the subject's sexual partner(s). In some embodiments, the at least one sexual partner of the subject may be a male or a female.

Some embodiments are directed to a method of reducing the incidence and/or risk of a preterm birth. Bacterial vaginosis infections may increase the risk of a preterm birth in a subject. In some embodiments, a method of reducing the incidence and/or risk of a preterm birth in a subject comprises administering to the subject a therapeutically effective amount of the compound of formula I, a prodrug thereof, a hydrate thereof, a solvate thereof, a polymorph thereof, or a pharmaceutically acceptable salt thereof.

In some embodiments, treatment of bacterial vaginosis, trichomoniasis, amoebiasis, giardiasis, or a combination thereof with the compound of formula I, a prodrug thereof, a hydrate thereof, a solvate thereof, a polymorph thereof, or a pharmaceutically acceptable salt thereof results in better than expected efficacy compared with FDA approved drugs used in the treatment of bacterial vaginosis, trichomoniasis, amoebiasis, giardiasis, or a combination thereof. In some embodiments, treatment of bacterial vaginosis, trichomoniasis, amoebiasis, giardiasis, or a combination thereof with the compound of formula I, a prodrug thereof, a hydrate thereof, a solvate thereof, a polymorph thereof, or a pharmaceutically acceptable salt thereof results in a higher rate of clinical cure than FDA-approved drugs used in the treatment of bacterial vaginosis, trichomoniasis, amoebiasis, giardiasis, or a combination thereof. For example, in some embodiments, the pharmaceutical compositions of the present invention provide a higher rate of clinical cure after treatment for a certain number of days as compared to other FDA approved drugs for the treatment of bacterial vaginosis, trichomoniasis, amoebiasis, giardiasis, or a combination thereof. In some embodiments, pharmaceutical compositions of the present invention provide a clinical cure in lesser number of days as compared to other FDA approved drugs for the treatment of bacterial vaginosis, trichomoniasis, amoebiasis, giardiasis, or a combination thereof. In some embodiments, the pharmaceutical compositions of the present invention provide a clinical cure in lesser dosage amount as compared to other FDA approved drugs for the treatment of bacterial vaginosis, trichomoniasis, amoebiasis, giardiasis, or a combination thereof. In some embodiments, the pharmaceutical compositions of the present invention provide a clinical cure with fewer adverse effects as compared to other FDA approved drugs for the treatment of bacterial vaginosis, trichomoniasis, amoebiasis, giardiasis, or a combination thereof. In some embodiments, treatment of bacterial vaginosis, trichomoniasis, amoebiasis, giardiasis, or a combination thereof with the compound of formula I, a prodrug thereof, a hydrate thereof, a solvate thereof, a polymorph thereof, or a pharmaceutically acceptable salt thereof results in a superior safety profile compared with FDA approved drugs used in the treatment of bacterial vaginosis, trichomoniasis, amoebiasis, giardiasis, or a combination thereof.

Some embodiments of the present invention are directed to a method of reducing the incidence and/or risk of a subject transmitting HIV to a sexual partner. Bacterial vaginosis infections may increase the risk of a HIV transmission to sexual partner. In some embodiments, the present invention includes a method of reducing the incidence and/or risk of the subject transmitting HIV to a sexual partner in a subject comprises administering to the subject a therapeutically effective amount of the compound of formula I, a prodrug thereof, a hydrate thereof, a solvate thereof, a polymorph thereof, or a pharmaceutically acceptable salt thereof.

Some embodiments are directed to a method of reducing the incidence and/or risk of a subject acquiring a sexually transmitted infection from a sexual partner. Some embodiments are directed to a method of reducing the incidence and/or risk of a subject transmitting a sexually transmitted infection to a sexual partner. Bacterial vaginosis infections may increase the risk of transmitting an STI or acquiring an STI from a sexual partner. In some embodiments, STI's include, but are not limited to chlamydia, gonorrhea, trichomoniasis, HSV-2, HIV, and HPV. In some embodiments the present invention is related to a method of reducing the incidence and/or risk of a subject acquiring a sexually transmitted infection from sexual partner including administering to the subject a therapeutically effective amount of the compound of formula I, a prodrug thereof, a hydrate thereof, a solvate thereof, a polymorph thereof, or a pharmaceutically acceptable salt thereof. In some embodiments the present invention is related to a method of reducing the incidence and/or risk of a subject transmitting a sexually transmitted infection (STI) to a sexual partner including administering to the subject a therapeutically effective amount of the compound of formula I, a prodrug thereof, a hydrate thereof, a solvate thereof, a polymorph thereof, or a pharmaceutically acceptable salt thereof.

In some embodiments, the use of the compound of formula I, a prodrug thereof, a hydrate thereof, a solvate thereof, a polymorph thereof, or a pharmaceutically acceptable salt thereof provides increase in the elimination half-life and/or a reduction in efficacious dose. In another embodiment, use of the compound of formula I, a prodrug thereof, a hydrate thereof, a solvate thereof, a polymorph thereof, or a pharmaceutically acceptable salt thereof reduces adverse side-effects. In another embodiment, the compound of formula I, a prodrug thereof, a hydrate thereof, a solvate thereof, a polymorph thereof, or a pharmaceutically acceptable salt thereof maintains the beneficial aspects of the non-deuterated secnidazole while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

As previously, mentioned, the present invention relates to a method for treating trichomoniasis in a subject in need thereof. The method includes selecting a subject in need of treatment for trichomoniasis and administering, to the subject, a therapeutically effective amount of the compound of formula I, a prodrug thereof, a hydrate thereof, a solvate thereof, a polymorph thereof, or a pharmaceutically acceptable salt thereof. In one embodiment, the method includes administering to the subject a pharmaceutical composition including a therapeutically effective amount of the compound of formula I, a prodrug thereof, a hydrate thereof, a solvate thereof, a polymorph thereof, or a pharmaceutically acceptable salt thereof.

Trichomoniasis is a genitourinary infection with the protozoan *Trichomonas vaginalis*. It is the most common non-viral sexually transmitted disease ("STD") worldwide. Women are affected more often than men. Trichomoniasis is one of the three major causes of vaginal complaints among reproductive aged women, along with bacterial vaginosis and candida vulvovaginitis, and a cause of urethritis in men; however, the infection is often asymptomatic.

In some embodiments, a method of treating trichomoniasis in a subject comprises co-administering to the subject a dose of the compound of formula I, a prodrug thereof, a hydrate thereof, a solvate thereof, a polymorph thereof, or a pharmaceutically acceptable salt thereof and an additional compound selected from ethinyl estradiol (EE2), norethindrone (NET), or a combination thereof. In some embodiments, the additional compound is co-administered on the same day as the compound of formula I, a prodrug thereof, a hydrate thereof, a solvate thereof, a polymorph thereof, or a pharmaceutically acceptable salt thereof. In some embodiments, the additional compound is administered on a different day than the compound of formula I, a prodrug thereof, a hydrate thereof, a solvate thereof, a polymorph thereof, or a pharmaceutically acceptable salt thereof. In some embodiments, the compound of formula I, a prodrug thereof, a hydrate thereof, a solvate thereof, a polymorph thereof, or a pharmaceutically acceptable salt thereof does not affect the contraceptive efficacy of the additional compound.

In some embodiments, the subject is a human. In yet other embodiments, the subject is a human female. In some embodiments, the human female is of an age ranging from a postmenarchal adolescent to a premenopausal woman. In some embodiments, the subject is an otherwise healthy female. In some embodiments, the subject is a pregnant female. In some embodiments, the subject is an otherwise healthy pregnant female. In some embodiments, the subject is a female with confirmed trichomoniasis. In some embodiments, the subject is a female with suspected trichomoniasis.

In some embodiments, the subject is a female presenting with purulent malodorous discharge (associated with burning, pruritus, dysuria, frequency, lower abdominal pain), dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, an elevated vaginal pH (about 5.0 to about 6.0), and any combination thereof. In some embodiments, the subject is asymptomatic. In some embodiments, the subject is a female with confirmed trichomoniasis. In some embodiments, the diagnosis of *Trichomonas vaginalis* is confirmed by laboratory testing (including, but not limited to motile trichomonads on wet mount, positive culture, increase in polymorphonuclear leukocytes, positive nucleic acid amplification test, or positive rapid antigen, nucleic acid probe test cervical cytology or any combination thereof). Microscopy (such as, but not limited to culture on Diamond's medium) is a key step in the evaluation of vaginal discharge, and is often the first step in the diagnostic evaluation for trichomoniasis. Microscopy is convenient and low cost. In some embodiments, nucleic acid amplification tests ("NAAT") can then be done for subjects with non-diagnostic (or negative) wet mounts. In some embodiments, if NAAT is not available, rapid diagnostic kits or culture are then performed. Additional laboratory tests include but are not limited to the APTIMA *Trichomonas vaginalis* assay; the APTIMA TV assay; the Amplicor assay (PCR assay for detection of *N. gonorrhoeae* and *C. trachomatis* that has been modified to detect *T. vaginalis* in vaginal/endocervical swabs or urine); NuSwab VG or any combination thereof; positive rapid antigen, nucleic acid probe test include but are not limited to the Affirm VP III Microbial Identification System; and the OSOM *Trichomonas* Rapid Test. In some embodiments, the subject is a female with suspected trichomoniasis. In some embodiments, suspected trichomoniasis is indicated by the presence of purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof.

In some embodiments, a method of treating trichomoniasis in a subject further comprises determining a post treatment clinical outcome. In some embodiments, a post treatment clinical outcome is indicative of a clinical outcome responder. In some embodiments, a clinical outcome responder is a subject that is asymptomatic. In some embodiments, a clinical outcome responder is a subject with normal vaginal discharge, normal vaginal pH, normal laboratory testing results (including, but not limited to the absence of motile trichomonads on wet mount, negative culture, normal polymorphonuclear leukocytes, negative nucleic acid amplification test, negative rapid antigen, negative nucleic acid probe test, negative rapid diagnostic kits or culture, negative cervical cytology, or any combination thereof) after treatment with a formulation comprising deuterated secnidazole or a pharmaceutically acceptable salt thereof. In some embodiments, a clinical outcome responder is a subject with without purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof.

In some embodiments, a post-treatment clinical outcome is observable after about 24 hours after administration. In some embodiments, a post-treatment clinical outcome is observable after about 48 hours after administration. In some embodiments, a post-treatment clinical outcome is observable after about 72 hours after administration. In some embodiments, a post-treatment clinical outcome is observable after about 96 hours after administration. In some embodiments, a post-treatment clinical outcome is observable after about 120 hours after administration. In some embodiments, a post-treatment clinical outcome is observable after about 168 hours after administration. In some embodiments, a post-treatment clinical outcome is observable after about 7 to about 10 days after administration. In some embodiments, a post-treatment clinical outcome is observable after about 11 to about 20 days after administration. In some embodiments, a post-treatment clinical outcome is observable after about 21 to about 30 days after administration.

In some embodiments, a method of treating trichomoniasis further comprises alleviation of one or more symptoms of trichomoniasis within up to about three days after administration to the subject. In some embodiments, a method of treating trichomoniasis further comprises an alleviation of one or more symptoms of trichomoniasis within up to about three days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, alleviation refers to a lessening of the severity of one or more symptoms. In some embodiments, alleviation of one or more symptoms of trichomoniasis occurs within about 24 hours after administration. In some embodiments, alleviation of one or more symptoms of trichomoniasis occurs within about 48 hours after administration. In some embodiments, alleviation of one or more symptoms of trichomoniasis occurs within about 72 hours after administration to the subject. In some embodiments, alleviation of one or more symptoms of trichomoniasis occurs within about 96 hours after administration to the subject. In some embodiments, alleviation of one or more symptoms of trichomoniasis occurs within about 120 hours after administration to the subject. In some embodiments, alleviation of one or more symptoms of trichomoniasis occurs within about 168 hours after administration to the subject. In some embodiments, alleviation of one or more symptoms of trichomoniasis occurs within about 7 to about 10 days after administration to the subject. In some embodiments, alleviation of one or more symptoms of trichomoniasis occurs within about 11 to about 20 days after administration to the subject. In some embodiments, alleviation of one or more symptoms of trichomoniasis occurs within about 21 to about 30 days after administration to the subject.

In some embodiments, a method of treating trichomoniasis further comprises a resolution of one or more symptoms of trichomoniasis within up to about seven days after administration to the subject. In some embodiments, a method of treating trichomoniasis further comprises a resolution of one or more symptoms of trichomoniasis within up to about seven days after administration to the subject. In some embodiments, the one or more symptoms include, but are not limited to, purulent malodorous discharge (associated with burning, pruritus, dysuria, frequency, lower abdominal pain), or dyspareunia, burning postcoital bleeding, dyspareunia, dysuria, a thin green-yellow frothy discharge, vulvovaginal erythema (erythema of the vulva and vaginal mucosa), punctate hemorrhages, urethritis, cystitis, purulent vaginitis, sequamative inflammatory vaginitis, atrophic vaginitis, erosive lichen planus, elevated vaginal pH (about 5.0 to about 6.0), and any combination thereof. In some embodiments, resolution of one or more symptoms of trichomoniasis occurs within about 24 hours after administration to the subject. In some embodiments, resolution of one or more symptoms of trichomoniasis occurs within about 48 hours after administration. In some embodiments, resolution of one or more symptoms of trichomoniasis occurs within about 72 hours after administration to the subject. In some embodiments, resolution of one or more symptoms of trichomoniasis occurs within about 96 hours after administration to the subject. In some embodiments, resolution of one or more symptoms of trichomoniasis occurs within about 120 hours after administration to the subject. In some embodiments, resolution of one or more symptoms of trichomoniasis occurs within about 168 hours after administration to the subject. In some embodiments, resolution of one or more symptoms of trichomoniasis occurs within about 7 to about 10 days after administration to the subject. In some embodiments, resolution of one or more symptoms of trichomoniasis occurs within about 11 to about 20 days after administration to the subject. In some embodiments, resolution of one or more symptoms of trichomoniasis occurs within about 21 to about 30 days after administration to the subject.

In some embodiments, treatment of trichomoniasis the compound of formula I, a prodrug thereof, a hydrate thereof, a solvate thereof, a polymorph thereof, or a pharmaceutically acceptable salt thereof results in better than expected efficacy compared with FDA approved drugs used in the treatment of trichomoniasis. In some embodiments, treatment of trichomoniasis with the compound of formula I, a prodrug thereof, a hydrate thereof, a solvate thereof, a polymorph thereof, or a pharmaceutically acceptable salt thereof results in a higher rate of clinical cure than FDA-approved drugs used in the treatment of trichomoniasis. For example, in some embodiments, the compound of formula I, a prodrug thereof, a hydrate thereof, a solvate thereof, a polymorph thereof, or a pharmaceutically acceptable salt thereof provides a higher rate of clinical cure after treatment for a certain number of days as compared to other FDA approved drugs for the treatment of trichomoniasis. In some embodiments, the compound of formula I, a prodrug thereof, a hydrate thereof, a solvate thereof, a polymorph thereof, or a pharmaceutically acceptable salt thereof provides a clinical cure in lesser number of days as compared to other FDA approved drugs for the treatment of trichomoniasis. In some embodiments, the compound of formula I, a prodrug thereof, a hydrate thereof, a solvate thereof, a polymorph thereof, or a pharmaceutically acceptable salt thereof provides a clinical cure in lesser dosage amount as compared to other FDA approved drugs for the treatment of trichomoniasis. In some embodiments, the compound of formula I, a prodrug thereof, a hydrate thereof, a solvate thereof, a polymorph thereof, or a pharmaceutically acceptable salt thereof provides a clinical cure with fewer adverse effects as compared to other FDA approved drugs for the treatment of trichomoniasis. In some embodiments, treatment of trichomoniasis with the compound of formula I, a prodrug thereof, a hydrate thereof, a solvate thereof, a polymorph thereof, or a pharmaceutically acceptable salt thereof results in a superior safety profile compared with FDA approved drugs used in the treatment of trichomoniasis.

In some embodiments, a method of treating trichomoniasis in a subject in need thereof further comprises administering to at least one of the subject's sexual partners, a therapeutically effective amount of the compound of formula I, a prodrug thereof, a hydrate thereof, a solvate thereof, a polymorph thereof, or a pharmaceutically acceptable salt thereof.

The pharmaceutical compositions of the present invention can take any of a variety of known forms that are suitable for a particular mode of administration. Exemplary modes of administration include, without limitation, orally, topically, transdermally, parenterally, subcutaneously, intravenous injection, intra-arterial injection, intramuscular injection, intraplurally, intraperitoneally, by intracavitary or intravesical instillation, intraocularly, intraventricularly, intralesionally, intraspinally, or by application to mucous membranes, such as, that of the nose, throat, and bronchial tubes. Preferred routes for administration include via oral, vaginal, topical (including buccal and sublingual), or parenteral (including subcutaneous, intramuscular, intravenous, intradermal, intratracheal, and epidural) administration. Also, preferred routes of administration would be those suitable for dosage forms such as tablets, capsules, softgels, microgranules, creams, gels, ovules, suppositories or other dosage forms available to those skilled in the art.

In some embodiments, the compound of formula I, a prodrug thereof, a hydrate thereof, a solvate thereof, a polymorph thereof, or a pharmaceutically acceptable salt thereof and the pharmaceutical compositions of the present invention may be mixed, stirred, or otherwise integrated into a food substance. In some embodiments, the food substance may be a liquid food, semisolid food, or soft food. In some embodiments, the food substance may include, but is not limited to applesauce, pudding, yogurt or the like. In some embodiments, integration of the secnidazole microgranule formulation into a food substance has a taste masking function. In some embodiments, the compound of formula I, a prodrug thereof, a hydrate thereof, a solvate thereof, a polymorph thereof, or a pharmaceutically acceptable salt thereof and the pharmaceutical compositions of the present invention may be mixed, stirred, or otherwise integrated in a liquid, such as water, juice, milk or the like.

The pharmaceutical forms suitable for injectable use (e.g., intravenous, intra-arterial, intramuscular, etc.) include sterile aqueous solutions or dispersions and sterile powders for the extemporaneous preparation of sterile injectable solutions or dispersions. The form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to, sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Oral dosage formulations can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

For parenteral administration, aqueous solutions in water-soluble form can be used to deliver one or more of the active agents. Additionally, suspensions of the active agent(s) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

In addition to the formulations described previously, the active agent(s) may also be formulated as a depot preparation. Such long acting formulations may be administered by implantation (e.g., subcutaneously or intramuscularly) or by intramuscular injection. Thus, for example, the active agent(s) may be formulated with suitable polymeric or hydrophobic materials (e.g., as an emulsion in an acceptable oil) or ion exchange resins, or as sparingly soluble derivatives (e.g., as a sparingly soluble salt). Selection of polymeric matrix material is based on biocompatibility, biodegradability, mechanical properties, cosmetic appearance, and interface properties. The particular application of the active agent(s) will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate, as well as other materials that are known in the drug delivery arts. The bioceramics may be altered in composition, such as in calcium-aluminate-phosphate and processing to alter pore size, particle size, particle shape, and biodegradability.

The pharmaceutical compositions may conveniently be presented in unit dosage form and may be prepared by conventional pharmaceutical techniques. Such techniques include the step of associating the active ingredient, i.e., deuterated secnidazole, and a pharmaceutical carrier(s) or excipient(s). In general, the compositions are prepared by uniformly and intimately associating the active ingredient with liquid carriers or finely divided solid carriers or both, and then, if necessary, shaping the product.

Compositions of the present invention suitable for oral administration may be presented as discrete units such as capsules, cachets, softgels, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc. A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

In another embodiment, pharmaceutical compositions which can be administered orally as push-fit capsules made of gelatin, as well as soft, sealed capsules made of gelatin and a plasticizer, such as glycerol or sorbitol. All formulations for oral administration should be in dosages suitable for such administration. The push-fit capsules can contain deuterated secnidazole in admixture with filler such as lactose, binders such as starches, and/or lubricants such as talc or magnesium stearate and, optionally, stabilizers. In soft capsules, deuterated secnidazole may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of deuterated secnidazole doses.

Compositions suitable for oral administration include lozenges comprising the ingredients in a flavored basis, usually sucrose and acacia or tragacanth; pastilles comprising the active ingredient in an inert basis such as gelatin and glycerin, or sucrose and acacia; and liquids comprising the ingredient to be administered in a suitable liquid carrier.

Compositions suitable for topical administration to the skin may be presented as ointments, creams, gels and pastes comprising the ingredient to be administered in a pharmaceutically acceptable carrier. Formulations for vaginal administration may be presented as a suppository with a suitable base comprising, for example, cocoa butter or a salicylate. Formulations suitable for vaginal administration may be presented as ovules, pessaries, tamports, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question, for example, those suitable for oral administration may include flavoring agents.

One embodiment of the present invention involves administering a single dose of therapeutically effective amount of the compound of formula I, a prodrug thereof, a hydrate thereof, a solvate thereof, a polymorph thereof, or a pharmaceutically acceptable salt thereof. Another embodiment of the present invention involves administering multiple doses at predetermined intervals, such as, but not limited to once a week, bi-weekly, monthly, bimonthly for the duration of treatment. In some embodiments, the duration of treatment may be at least one week. In some embodiments, the duration of treatment may be at least one month. In some embodiments, the duration of treatment is about six months.

The above-identified active agents, including deuterated secnidazole or pharmaceutically acceptable salts thereof, are to be administered in an amount effective to achieve their intended purpose (i.e., to treat infection, treat a subject at risk for infection). While individual needs vary, determination of optimal ranges of effective amounts of each component is within the skill of the art. The quantity administered will vary depending on the patient and the mode of administration and can be any effective amount. In one embodiment, a typical dosage may include about 0.1 to about 3000 mg. In another embodiment, the preferred dosage may include about 1 to about 2000 mg, about 100 mg to about 1500 mg, about 500 mg to about 1000 mg. However, because patients respond differently to therapies, monitoring of the treatment efficacy should be conducted, allowing for adjustment of the dosages as needed. Treatment regimen for the administration of the above-identified active agents of the present invention can also be determined readily by those with ordinary skill in art.

The selection of the specific dose regimen may be adjusted or titrated by the clinician according to methods known to the clinician in order to obtain the optimal clinical response. The amount of the compound of formula I, a prodrug thereof, a hydrate thereof, a solvate thereof, a polymorph thereof, or a pharmaceutically acceptable salt thereof to be administered may be that amount which is therapeutically effective. The dosage to be administered may depend on the characteristics of the subject being treated, e.g., the particular animal or human subject treated, age, weight, body mass index, body surface area, health, types of concurrent treatment, if any, and frequency of treatments, and can be easily determined by one of skill in the art (e.g., by the clinician).

Individual components or a combination of components of the compositions described in the present invention can be present in any physical form. For example, the present invention provides for a pharmaceutical composition where at least one of the components of the composition is present within the composition in solid, liquid, particulate, colloidal, suspension, emulsion, liquid sol, gel, solid sol form. In yet another embodiment, compositions of deuterated secnidazole disclosed herein suitable for oral administration may be presented as discrete units such as capsules, cachets or tablets each containing a predetermined amount of deuterated secnidazole; as a powder or granules; as a solution or a suspension in an aqueous liquid or a non-aqueous liquid; or as an oil-in-water liquid emulsion or a water-in-oil liquid emulsion. The deuterated secnidazole may also be presented as a bolus, electuary or paste.

The deuterated secnidazole, pharmaceutically acceptable salts thereof, and/or the pharmaceutical compositions disclosed herein may be in the form of a microgranule formulation. In some embodiments, the microgranule formulation comprises a plurality of microgranules. In some embodiments, the plurality of microgranules have a particle size range of about 100 to about 900 micrometers. In some embodiments, the plurality of microgranules have a particle size range of about 200 to about 800 micrometers. In some embodiments, the plurality of microgranules have a particle size range of about 300 to about 700 micrometers. In some embodiments, the plurality of microgranules have a particle size range of about 400 to about 600 micrometers. In some embodiments, the plurality of microgranules have a particle size of about 100 micrometers, 150 micrometers, 200 micrometers, 250 micrometers, 300 micrometers, 350 micrometers, 400 micrometers, 450 micrometers, 500 micrometers, 550 micrometers, or 600 micrometers.

In some embodiments, the plurality microgranules has a volume-weighted particle size distribution within a microgranule population, wherein the volume-weighted particle size distribution as measured from a representative sample of the microgranule population includes:
  (a) 10% of the microgranule population has a volume-weighted particle size about no less than 470 micrometers;
  (b) 50% of the microgranule population has a volume-weighted particle size between about no less than 640 micrometers and about no more than 810 micrometers;
  (c) 90% of the rogranule population has a volume-weighted particle size about no more than 1170 micrometers; or
  (d) a combination thereof, which can include some or all of (a) through (c) above.

As used herein, the term "volume-weighted particle size distribution" refers to a distribution where the contribution of each particle in the distribution relates to the volume of the particle (equivalent to the mass if the density is uniform), i.e., the particles contribution will be proportional to its size (see, e.g., Powder Sampling and Particle Size Determination by T. Allen, $1^{st}$ Edition., Elsevier Science, 2003 and Particle Size Measurement by T. Allen, Chapman & Hall, $4^{th}$ Edition, 1992). Static light scattering techniques such as laser diffraction and other techniques known in the art can be used to determine volume-weighted particle size distribution.

In some embodiments, the microgranule formulation comprises at least one of sugar spheres, povidone, polyethylene glycol 4000, ethyl acrylate-methyl methacrylate copolymer (sold under the trademark Eudragit NE30D), talc, colloidal silicon dioxide, or a combination thereof. In some embodiments, the plurality of microgranules are white to off-white in color.

In some embodiments of the present invention, the deuterated secnidazole, pharmaceutically acceptable salts thereof, and/or the pharmaceutical compositions disclosed herein may be in the form of a vaginal suppository. The term "vaginal suppository" refers to a solid dosage form that is inserted in to a subject's vagina where the suppository dissolves or melts and exerts local or systemic effects. In some embodiments, the vaginal suppository contains deuterated secnidazole, pharmaceutically acceptable salts thereof, and/or the pharmaceutical compositions disclosed herein. The vaginal suppository has physical properties, such as shape, size and consistency that facilitate its therapeutic use via intravaginal administration.

In one embodiment, the vaginal suppository of the present invention includes a mixture of deuterated secnidazole with, e.g., a hard fat wherein the mixture can be a homogenous mixture or a heterogeneous mixture and shaped in the form of a vaginal suppository. The combination can be homogenously dispersed within the vaginal suppository or can be positioned in a portion of the vaginal suppository. For example, the combination could be homogenously dispersed within, e.g., a fatty or oily base of the suppository or could be located in the outer portion or core of the suppository. In another embodiment, the combination may be present or absent in different layers or portions of the vaginal suppository. In some embodiments, the concentration of the composition could be varied between layers of the vaginal suppository in order to achieve a target pharmacokinetic profile of the combination.

In another embodiment, all of the particles of the pharmaceutical compositions of the present invention are included in a vaginal suppository and can be for example, distributed homogenously within the vaginal suppository or present in a layer or a portion of the suppository. The vaginal suppositories of the present invention can be prepared not just by using components of the pharmaceutical compositions in particulate form but also by other methods available in the art, for example, by dissolving the components of the pharmaceutical composition in a base used for forming the vaginal suppositories. The suppository can also be formed by melting one or more components of the pharmaceutical composition of the present invention and dissolving the other components in the molten component(s).

In another embodiment, the vaginal suppository of the present invention may have any shape suitable for administration. For instance, it can have a smooth torpedo shape or a bullet shape. In one embodiment, the pharmaceutical composition is such that it dissolves or melts at about 37° C. or melts or dissolves in a patient's body. In one embodiment, the vaginal suppository is formed using a base, such as a fatty or oily base, that melts at about 37° C. or melts in a patient's body.

In another embodiment, the vaginal suppository includes deuterated secnidazole or pharmaceutically acceptable salt thereof and one or more oily or fatty bases. In yet another embodiment, the vaginal suppository includes deuterated secnidazole or pharmaceutically acceptable salt thereof, one or more oily or fatty bases, and one or more emulsifying agents. In yet another embodiment, the vaginal suppository includes deuterated secnidazole or pharmaceutically acceptable salt thereof, one or more oily or fatty bases, one or more emulsifying agents, and one or more antioxidants.

Fatty or oily bases can be used as base for the vaginal suppository of the present invention. Suitable fatty or oily bases include, without limitation, theobroma oil, coconut oil, cocoa butter, lauric oil, beef tallow, a hard fat, glyceride of a fatty acid, glycerol-gelatin bases, or a combination thereof.

Suitable emulsifying agent for use in the pharmaceutical compositions of the present invention is, for example, a surfactant. Exemplary emulsifying agents include, but are not limited to, glyceryl laurate, ceteth-2, polyethylene glycol-30 ("PEG-30") dipolyhydroxystearate, glyceryl stearate SE, sorbitan stearate, sucrose cocoate, PEG-4 dilaurate, methyl glucose sesquistearate, lecithin, PEG-8 dioleate, sorbitan laurate, PEG-40 sorbitan peroleate, laureth-4, PEG-7 glycerol cocoate, PEG-20 almond glycerides or combinations thereof.

Suitable antioxidants for the present invention, include, without limitation, butylated hydroxy toluene ("BHT"), butylated hydroxy anisole ("BHA"), sodium ascorbate, tocopherol acetate, propyl gallate, lecithin, Vitamin E tocopherol, sesamin, sesamol, sesamolin, alpha tocopherol, ascorbic acid, ascorbyl palmitate, fumaric acid, malic acid, and sodium metabisulphite, disodium ethylenediaminetetracetic acid ("EDTA"), and combinations of any of the foregoing.

In some embodiments of the present invention, the deuterated secnidazole, pharmaceutically acceptable salts thereof, and/or the pharmaceutical compositions disclosed herein may be in the form of a taste-masked dosage form. In some embodiments, the taste-masked formulation is in the form of, e.g. a tablet or microgranule formulation. Methods of taste masking that are readily available in the art, such as coating, and can be used on the tablet or microgranule formulations. For example, taste masking of a microgranule formulation containing an Active Pharmaceutical Ingredient ("API") can be done by coating, e.g., each of the microgranules containing an API.

In some embodiments of the present invention, the deuterated secnidazole, pharmaceutically acceptable salts thereof, and/or the pharmaceutical compositions disclosed herein may be in the form of a soft gelatin capsule or ovule form for intravaginal administration. In some embodiments, the soft gelatin capsule is for vaginal administration of deuterated secnidazole and includes a soft gelatin capsule and a therapeutically effective amount of deuterated secnidazole dispersed in a mono unsaturated fatty acid excipient.

The contents of soft gelatin capsule compositions of the present invention may be solid or liquid at room temperature, and preferably have a flow point in the range of 30 to 40° C.; more preferably 30 to 37° C. The flow point is visually determined based upon heating a sample from 25° C. at a rate of 2° C. per minute and observing the temperature at which rapid flow of the sample occurs. This measurement is conveniently carried out using a microscope equipped with a video camera having on-screen digital monitoring of the temperature. In some embodiments the contents of the soft gelatin capsule compositions may be liquid at room temperature.

The soft gelatin capsule compositions of the present invention may also contain additives, such as stabilizers (e.g., antioxidants and other types of preservatives), polymorphic transition accelerators (e.g., tristearin), biocompatible polymers, surfactants, dispersants, water absorbents and the like. The use of biocompatible polymers, surfactants and water absorbents are described in U.S. Pat. No. 4,765,978, the disclosure of which is hereby incorporated by reference. The concentration of these additives may vary according to the particular additive used and the desired result sought. The use of the kind and concentration of additives are well within the ability of the skilled artisan. The soft gelatin capsule compositions described herein may be prepared, packaged, or sold in bulk, as a single unit dose or as multiple unit doses and may be administered in the conventional manner by any route where they are active.

In some embodiments, therapeutically effective amounts, daily doses, or single unit doses of the deuterated secnidazole compositions described herein may be administered once per day or multiple times per day, such as 1 to 5 doses, twice per day or three times per day.

In some embodiments, the methods described herein may comprise a dosage regimen that may include a plurality of daily doses having an equal amount of deuterated secnidazole compound as the initial dose in one or more unit doses. In other embodiments, the dosage regimen may include an initial dose of deuterated secnidazole, such as, deuterated secnidazole compound in one or more unit doses, then a plurality of daily doses having a lower amount of deuterated secnidazole compound as the initial dose in one or more unit doses. The dosage regimen may administer an initial dose followed by one or more maintenance doses. The plurality of doses following the administering of an initial dose may be maintenance doses.

The following example illustrates aspects of the present invention, and is set forth to assist in understanding the present invention. This example should not be construed as specifically limiting the present invention described and claimed herein. Variations of the present invention, including the substitution of all equivalents now known or later developed, which would be within the purview of those skilled in the art, and changes in formulation or minor changes in experimental design, are considered to fall within the scope of the present invention and appended claims.

EXAMPLES

Example 1: Effect of Deuteration on Secnidazole Metabolism by Human Cytochrome $P_{450}$ Isoforms A study was conducted to determine the effect of deuteration on the metabolism of secnidazole by human cytochrome $P_{450}$ ("CYP") enzymes. The metabolism of α,2-dimethyl-5-nitro-1H-imidazole-1-ethanol-d3 ("secnidazole-d3") and α,2-dimethyl-5-nitro-1H-imidazole-1-ethanol-d6 ("secnidazole-d6"; see CAS No. 1346603-27-7) by cDNA-expressed CYP enzymes were investigated in vitro and compared to results obtained with undeuterated secnidazole.

A 600 µL reaction mixture containing enzyme protein, NADPH generating system (1.3 mM NADP+, 3.3 mM glucose-6-phosphate, 0.4 U/mL glucose-6-phosphate dehydrogenase, 3.3 mM magnesium chloride) and each test article (secnidazole, secnidazole-d3, or secnidazole-d6) at two concentrations (e.g. 1 µM and 10 µM) in 100 mM potassium phosphate (pH 7.4) was incubated at 37° C. At two time points (0 and 120 min), the reaction was stopped by removing an aliquot and combining it with an equal volume of cold acetonitrile containing an internal standard (labetalol) and placement on ice. Samples were centrifuged to pellet the protein and the supernatant was frozen at −20° C. for subsequent analysis by LC-MS/MS.

Protein concentrations were constant for all isoforms within an experiment and standardized by the addition of control microsomes. Incubations were performed in duplicate. Incubations with vector control enzyme preparations and without enzyme source were included as negative controls.

For the positive control coumarin (Cytochrome $P_{450}$ 2A6, otherwise known as "CYP2A6"), a 400 µL reaction mixture containing enzyme protein, NADPH generating system (1.3 mM NADP+, 3.3 mM glucose-6-phosphate, 0.4 U/mL glucose-6-phosphate dehydrogenase, 3.3 mM magnesium chloride) and one concentration of substrate in 100 mM potassium phosphate (pH 7.4) was incubated at 37° C. for 20 minutes (CYP2A6). The reaction was stopped by adding 100 µL of cold acetonitrile containing an internal standard (labetalol). The formation of 7-hydroxy coumarin was quantified based on a standard curve.

All other positive controls were assayed at one concentration in duplicate in accordance with the methods described above. The percent of parent remaining at the end of the incubation was compared to 0 min based on the peak area ratio of the substrate and internal standard.

LC-MS/MS methods for secnidazole, secnidazole-d3, and secnidazole-d6 using labetalol as the internal standard were developed. The fraction of parent compound remaining compared to 0 min was determined based on peak area ratio (analyte/internal standard). Additional MRMs for known or suspected metabolites (metabolite structures were provided) were monitored, but no signal above noise was detected for any of the 3 transitions.

Secnidazole, secnidazole-d3, and secnidazole-d6 at 1.0 µM and 10 µM were each incubated in the presence of cDNA-expressed CYP1A2, CYP2A6, CYP2B6, CYP2C8, CYP2C9, CYP2C19, CYP2D6, CYP2E1, CYP3A4, and CYP3A5 for 120 minutes. The average percent of parent compound remaining for all isoforms and concentrations was greater than 79% for secnidazole, greater than 96% for secnidazole-d3, and less than 100% for secnidazole-d6.

In particular, secnidazole at 10 µM showed loss when metabolized by cDNA-expressed CYP2C8 and CYP2C9, with 82% and 79% remaining, respectively. Unexpectedly, secnidazole-d3 and secnidazole-d6 did not demonstrate any depletion by cDNA-expressed CYP2C8 and CYP2C9 under those conditions.

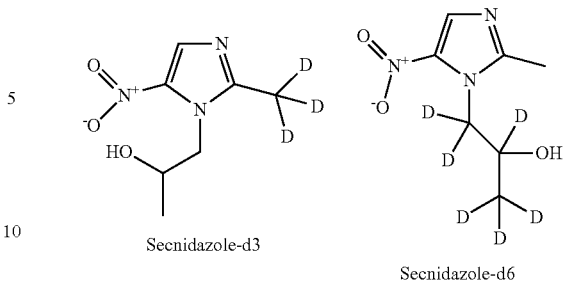

Secnidazole-d3

Secnidazole-d6

Example 2: Composition of Deuterated Secnidazole Granules

The following deuterated secnidazole granules were made using deuterated secnidazole. The composition of the granules includes a 1-gram dose of deuterated secnidazole.

| Component | Function | Quality Standard | Quantity, mg/1 g Dose |
|---|---|---|---|
| Compound I (Deuterated Secnidazole) | Active Ingredient | Manufacturer's specifications | 1000.00 |
| Sugar Spheres (size 35-40 mesh) | Inert core | NF | 940.00 |
| Povidone (Plasdone K-29/32) | Dispersion and binding | USP | 100.82 |
| Polyethylene Glycol 4000 | Seal coating | NF | 41.50 |
| Eudragit NE30D (Ethyl Acrylate Methyl Methacrylate Copolymer) | Modified release coating | NF | 138.30 |
| Talc | Anti-tacking agent | USP | 138.30 |
| Total | | | 2365.00 |

Example 3: Minimum Inhibitory Concentration ("MIC")

The MIC for the antimicrobial agents secnidazole (parent compound), secnidazole-D3 and secnidazole-D6 will be determined in connection with the following organisms: *Lactobacillus crispatus; Atopobium vaginae; Gardnerella vaginalis; Megasphaera phylotype; Prevotella amnii; Prevotella timonensis; Prevotella bivia*; and *Porphyromonas* species. MIC population distribution, MIC range and MIC50 and MIC90 values will also be determined.

Agar dilution testing for antimicrobial agents secnidazole (parent compound), secnidazole-D3 and secnidazole-D6 will be done conducted according to the guidelines in Clinical and Laboratory Standard Institute ("CLSI"), document M11-A8, entitled "Methods for Antimicrobial Susceptibility Testing for Anaerobic Bacteria—Eighth Edition." The organisms to be tested were isolated from the female genital tract of women with and without bacterial vaginosis in the Pittsburgh, PA area, and recovered between January 2013 and March 2015. Older isolates are also included in the testing.

Quality control will be monitored with the following organisms recommended by the CLSI guidelines and tested in parallel with the above-listed test organisms: ATCC 25285 *Bacteroides fragilis*; ATCC 29741 *Bacteroides*

*thetaiotamicron*; and ATCC 700057 *Clostridium difficile*. Additionally, *G. vaginalis* (ATCC 14018) will be added to all sets testing *G. vaginalis* isolates.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the present invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the present invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the present invention unless otherwise indicated herein or otherwise clearly contradicted by context.

In all of the foregoing embodiments disclosed herein, it is to be understood that all embodiments may be further limited by using "consisting of" or "consisting essentially of" language, rather than "comprising". When used, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A compound of formula I:

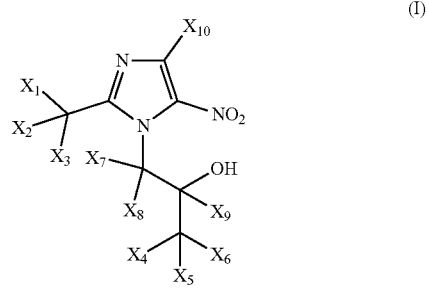

or a pharmaceutically acceptable salt thereof,
wherein $X_4$, $X_5$, and $X_6$ are deuterium, and
wherein $X_1$, $X_2$, $X_3$, $X_7$, $X_8$, $X_9$, and $X_{10}$ are hydrogen.

2. A pharmaceutical composition comprising (a) the compound of formula I, a pharmaceutically acceptable salt thereof of claim 1, or a combination thereof, and (b) at least one pharmaceutically acceptable carrier.

3. The pharmaceutical composition according to claim 2, wherein the amount of the compound of formula I, or the pharmaceutically acceptable salt thereof in the pharmaceutical composition is from about 0.1 mg to about 2000 mg.

4. The pharmaceutical composition according to claim 2, wherein the pharmaceutical composition is in the form of a tablet, granules, microgranules, vaginal suppository, soft gelatin capsule, taste-masked tablet, taste-masked granules, taste-masked microgranules, or a combination thereof.

5. The pharmaceutical composition according to claim 2, wherein the pharmaceutical composition is in the form of a plurality of granules, a plurality of microgranules, a plurality of taste-masked granules, a plurality of taste-masked microgranules, or a combination thereof.

6. The pharmaceutical composition according to any one of claims 2-5, further comprising at least one pharmaceutically acceptable excipient.

7. The pharmaceutical composition according to claim 6, wherein the pharmaceutically acceptable excipient is selected from a group consisting of an inert core, a dispersion agent, a binding agent, a coating agent, a modified release coating agent, an anti-tacking agent, and a combination thereof.

8. The pharmaceutical composition according to any one of claims 2-7, wherein the elimination half-life of the compound of formula I, or the pharmaceutically acceptable salt thereof is from about 29 hours to about 58 hours.

9. The pharmaceutical composition according to claim 8, wherein the elimination half-life of the compound of formula I, or the pharmaceutically acceptable salt thereof is from about 34 hours to about 58 hours.

10. A method for treating bacterial vaginosis, trichomoniasis, amoebiasis, giardiasis, or a combination thereof in a subject in need thereof comprising:
selecting the subject in need of treatment for bacterial vaginosis, trichomoniasis, amoebiasis, giardiasis, or a combination thereof; and
administering to the subject a therapeutically effective amount of a compound of formula I,
wherein the compound of formula I is:

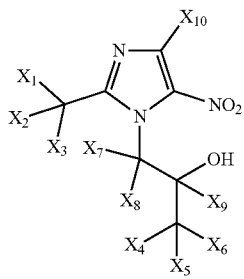

(I)

or a pharmaceutically acceptable salt thereof,
wherein $X_4$, $X_5$, and $X_6$ are deuterium, and
wherein $X_1$, $X_2$, $X_3$, $X_7$, $X_8$, $X_9$, and $X_{10}$ are hydrogen.

11. The method according to claim 10, wherein the subject is human female or a pregnant human female.

12. The method according to claim 10, wherein the therapeutically effective amount of compound of formula I is from about 0.1 mg to about 2000 mg.

13. The method according to claim 10, wherein the therapeutically effective amount of the compound of formula I is administered as a single dose.

14. The method according to any one of claim 10 or 11-13, wherein the therapeutically effective amount of the compound of formula I is administered orally.

15. The method according to any one of claim 10 or 11-14, wherein the therapeutically effective amount of the compound of formula I is co-administered with an additional compound selected from ethinyl estradiol (EE2), norethindrone (NET), and a combination thereof.

16. The method according to claim 15, wherein the compound of formula I does not affect the contraceptive efficacy of the additional compound.

17. The method according to any one of claim 10, 11-15 or 16, wherein the composition of formula I is in the form of a tablet, granules, microgranules, vaginal suppository, soft gelatin capsule, taste-masked tablet, taste-masked granules, taste-masked microgranules, or a combination thereof.

18. The method according to any one of claim 10, 11-15, 16 or 17, wherein the compound of formula I is in the form of a plurality of granules, a plurality of microgranules, a plurality of taste-masked granules, a plurality of taste-masked microgranules, or a combination thereof.

19. The method according to any one of claim 10, 11-15 or 16-18, wherein the compound of formula I is administered to the subject as a pharmaceutical composition.

20. The method according to claim 19, wherein the pharmaceutical composition further comprises at least one pharmaceutically acceptable excipient, at least one pharmaceutically acceptable carrier, or a combination thereof.

21. The method according to claim 20, wherein the pharmaceutically acceptable excipient is selected from the group consisting of an inert core, a dispersion agent, a binding agent, a coating agent, a modified release coating agent, an anti-tacking agent, and a combination thereof.

22. The method according to any one of claim 10, 11-15 or 16-21, wherein the elimination half-life of the compound of formula I or the pharmaceutically acceptable salt thereof is from about 29 hours to about 58 hours.

23. The method according to any one of claim 10, 11-15 or 16-22, wherein the elimination half-life of the compound of formula I, or the pharmaceutically acceptable salt thereof is from about 34 hours to about 58 hours.

* * * * *